United States Patent
Lippard et al.

(10) Patent No.: US 9,265,747 B2
(45) Date of Patent: Feb. 23, 2016

(54) PLATINUM (IV) COMPLEXES FOR USE IN DUAL MODE PHARMACEUTICAL THERAPY

(75) Inventors: Stephen J. Lippard, Cambridge, MA (US); Shanta Dhar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 688 days.

(21) Appl. No.: 13/060,354

(22) PCT Filed: Aug. 26, 2009

(86) PCT No.: PCT/US2009/004846
§ 371 (c)(1),
(2), (4) Date: May 16, 2011

(87) PCT Pub. No.: WO2010/027428
PCT Pub. Date: Mar. 11, 2010

(65) Prior Publication Data
US 2011/0257261 A1    Oct. 20, 2011

Related U.S. Application Data

(60) Provisional application No. 61/091,977, filed on Aug. 26, 2008, provisional application No. 61/196,419, filed on Oct. 17, 2008.

(51) Int. Cl.
| | | |
|---|---|---|
| *A61K 31/282* | (2006.01) | |
| *A61K 31/19* | (2006.01) | |
| *A61K 33/24* | (2006.01) | |
| *A61K 45/06* | (2006.01) | |

(52) U.S. Cl.
CPC ............... *A61K 31/282* (2013.01); *A61K 31/19* (2013.01); *A61K 33/24* (2013.01); *A61K 45/06* (2013.01)

(58) Field of Classification Search
CPC .............................. A61K 31/28; A61K 31/282
See application file for complete search history.

(56) References Cited

U.S. PATENT DOCUMENTS

| | | | |
|---|---|---|---|
| 4,843,161 | A | 6/1989 | Lippard et al. |
| 5,244,919 | A | 9/1993 | Abrams et al. |
| 6,806,289 | B1 | 10/2004 | Lippard et al. |
| 7,138,520 | B2 | 11/2006 | Lippard et al. |
| 7,232,919 | B2 | 6/2007 | Lal |
| 8,729,286 | B2 | 5/2014 | Lippard et al. |
| 2004/0235712 | A1 | 11/2004 | Lippard et al. |
| 2005/0090478 | A1 | 4/2005 | Barenholz et al. |
| 2007/0082882 | A1 | 4/2007 | Farrell |
| 2007/0104654 | A1 | 5/2007 | Hsieh et al. |
| 2007/0154398 | A1 | 7/2007 | Wang et al. |
| 2010/0330197 | A1 | 12/2010 | Higashiguchi et al. |
| 2011/0300219 | A1 | 12/2011 | Lippard et al. |
| 2013/0029959 | A1 | 1/2013 | Lippard et al. |
| 2013/0303606 | A1 | 11/2013 | Lippard et al. |
| 2014/0274988 | A1 | 9/2014 | Lippard et al. |
| 2014/0343139 | A1 | 11/2014 | Lippard et al. |

FOREIGN PATENT DOCUMENTS

| | | |
|---|---|---|
| DE | 19623746 A1 | 12/1997 |
| EP | 0 199 524 B1 | 2/1992 |
| EP | 0 679 656 A1 | 11/1995 |
| WO | WO 2005/092298 A1 | 10/2005 |
| WO | WO 2006/108276 A1 | 10/2006 |
| WO | WO 2007/021852 A2 | 2/2007 |
| WO | WO 2007/124314 A2 | 11/2007 |
| WO | WO 2007/133807 A2 | 11/2007 |
| WO | WO 2008/121949 A1 | 10/2008 |
| WO | WO 2009/032172 A2 | 3/2009 |
| WO | WO 2010/047765 A2 | 4/2010 |
| WO | WO 2010/150036 A1 | 12/2010 |
| WO | WO 2012/177935 A1 | 12/2012 |

OTHER PUBLICATIONS

He et al. PNAS, 2000, vol. 97, No. 11, pp. 5768-5772.*
Walker et al. Br. J. Cancer, 1991, vol. 64, pp. 764-768.*
Kallio et al. Apoptosis, 2005, vol. 10, pp. 1395-1410.*
Toogood, P. L. Current Opinion in Chemical Biology, Jul. 2008, pp. 457-463.*
Dhar et al., Mitaplatin, a potent fusion of cisplatin and the orphan drug dichloroacetate. Proc Natl Acad Sci U S A. Dec. 29, 2009;106(52):22199-204. doi: 10.1073/pnas.0912276106. Epub Dec. 10, 2009.
International Search Report and Written Opinion for PCT/US2008/010213 mailed Mar. 24, 2009.
International Preliminary Report on Patentability for PCT/US2008/010213 mailed Mar. 11, 2010.
International Search Report and Written Opinion for PCT/US2009/004846 mailed Dec. 8, 2009.
International Preliminary Report on Patentability for PCT/US2009/004846 mailed Mar. 10, 2011.
International Search Report and Written Opinion for PCT/US2009/005687 mailed May 26, 2010.
International Preliminary Report on Patentability for PCT/US2009/005687 mailed May 5, 2011.
International Search Report and Written Opinion for PCT/US2012/043620 mailed Sep. 28, 2012.
International Preliminary Report on Patentability for PCT/US2012/043620 mailed Jan. 9, 2014.
International Search Report and Written Opinion for PCT/US2012/043626 mailed Oct. 8, 2012.
International Preliminary Report on Patentability for PCT/US2012/043626 mailed Jan. 9, 2014.

(Continued)

*Primary Examiner* — Samira Jean-Louis
(74) *Attorney, Agent, or Firm* — Wolf, Greenfield & Sacks, P.C.

(57) ABSTRACT

The present invention provides compositions, preparations, formulations, kits, and methods useful for treating subjects in need of therapeutic protocol, including subjects having cancer or at risk of developing cancer. Some embodiments of the invention may comprise a composition comprising a first component comprising a precursor to a therapeutically active platinum agent and a precursor to a second therapeutically active agent. The therapeutically active platinum agent and the second therapeutically active agent may dissociate from each other, thereby forming a first therapeutically active platinum agent and a second therapeutically active agent. The second therapeutically active gent may affect a cellular pathway of a cancer cell and may be substantially inactive towards non-cancerous cells.

16 Claims, 5 Drawing Sheets

(56) References Cited

OTHER PUBLICATIONS

Al-Allaf et al., Platinum(II) and palladium(II) complexes analogous to oxaliplatin with different cyclohexyldicarboxylate isomeric anions and their in vitro antitumour activity. Structural elucidation of [Pt(C2O4)(cis-dach)]. Transition Metal Chemistry. 2003;28: 717-21.
Ang et al., Transcription inhibition by platinum-DNA cross-links in live mammalian cells. J Am Chem Soc. Jun. 2, 2010;132(21):7429-35. doi: 10.1021/ja101495v.
Bauer et al., Monofunctional platinum amine complexes destabilize DNA significantly. Eur J Biochem. Sep. 1, 1998;256(2):253-60.
Cohen et al., Binding of cis- and trans-dichlorodiammineplatinum(II) to DNA: evidence for unwinding and shortening of the double helix. Science. Mar. 9, 1979;203(4384):1014-6.
Comess et al., Replication inhibition and translesion synthesis on templates containing site-specifically placed cis-diamminedichloroplatinum(II) DNA adducts. Biochemistry. Apr. 28, 1992;31(16):3975-90.
Costello et al., Evidence for changes in RREB-1, ZIP3, and Zinc in the early development of pancreatic adenocarcinoma. J Gastrointest Cancer. Dec. 2012;43(4):570-8. doi: 10.1007/s12029-012-9378-1.
De Pascali et al., First Examples of β-Diketonate Platinum(II) Complexes with Sulfoxide Ligands. Eur Journal of Inorg Chem. Feb. 2005; (4): 788-96.
De Pascali et al., Mutagenic Tests Confirm That New Acetylacetonate Pt(II) Complexes Induce Apoptosis in Cancer Cells Interacting with Nongenomic Biological Targets. Met Based Drugs. 2011;2011:763436. doi: 10.1155/2011/763436. Epub Apr. 10, 2011.
Desoize et al., Particular aspects of platinum compounds used at present in cancer treatment. Crit Rev Oncol Hematol. Jun. 2002;42(3):317-25.
Dhar et al., Current Status and Mechanism of Action of Platinum-Based Anticancer Drugs. Bioinorganic Medicinal Chemistry, Enzo Alessio, Ed. Wi-ley-VCH Verlag GmbH & Co. KgaA. Weinheim, Germany, Chapter 3. 2010:79-95.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Dhar et al., Targeted single-wall carbon nanotube-mediated Pt(IV) prodrug delivery using folate as a homing device. J Am Chem Soc. Aug. 27, 2008;130(34):11467-76. doi: 10.1021/ja803036e. Epub Jul. 29, 2008.
Dorwald, Side Reactions in Organic Synthesis: A Guide to Successful Design. Wiley VCH GmbH & Co. KGaA. 2005. pp. 1-15.
Feazell et al., Soluble single-walled carbon nanotubes as longboat delivery systems for platinum(IV) anticancer drug design. J Am Chem Soc. Jul. 11, 2007;129(27):8438-9. Epub Jun. 15, 2007.
Fink et al., In vitro and in vivo resistance to cisplatin in cells that have lost DNA mismatch repair. Cancer Res. May 15, 1997;57(10):1841-5.
Fink et al., The role of DNA mismatch repair in platinum drug resistance. Cancer Res. Nov. 1, 1996;56(21):4881-6.
Giandomenico et al., Carboxylation of Kinetically Inert Platinum(IV) Hydroxy Complexes. An Entr.acte.ee into Orally Active Platinum(IV) Antitumor Agents. Inorg Chem. Mar. 1995;34(5):1015-21. doi: 10.1021/ic00109a004.
Gill et al., Synthese, kinetics and mechanism of formation of polynuclear hydroxo-bridged complexes of (trans-1,2-diaminocyclohexane)platinum(II). J Am Chem Soc. 1982;104:4598-604.
Graf et al., Platinum(IV)-chlorotoxin (CTX) conjugates for targeting cancer cells. J Inorg Biochem. May 2012;110:58-63. doi: 10.1016/j.jinorgbio.2012.02.012. Epub Feb. 23, 2012.
Hall et al., Basis for design and development of platinum(IV) anticancer complexes. J Med Chem. Jul. 26, 2007;50(15):3403-11. Epub Jun. 28, 2007.

Hoeschele et al., Synthesis and characterization of diastereomeric (substituted iminodiacetato)(1,2-diaminocyclohexane)platinum(II) complexess. Inorganic Chemistry. 1988;27:4106-13.
Hollis et al., Chemical and biological properties of a new series of cis-diammineplatinum(II) antitumor agents containing three nitrogen donors: cis-[Pt(NH3)2(N-donor)Cl]+. J Med Chem. Jan. 1989;32(1):128-36.
Hollis et al., Mechanistic studies of a novel class of trisubstituted platinum(II) antitumor agents. Cancer Res. Apr. 1, 1991;51(7):1866-75.
Hollis et al., Synthesis and Structures of Platinum(III) Complexes of α-Pyridone, [X(NH3)2Pt(C5H4NO)2Pt(NH3)2X](NO3)2*$n$H2O (X- = Cl-, NO2-, Br-). Inorg Chem. 1983;22:3637-44.
Howe-Grant et al., Aqueous Platinum (II) Chemistry; Binding to Biological Molecules. Metal Ions in Biological Systems. Sigel et al., eds. 1980;11:63-125.
Ivanov et al., Biological activity of platinum (II) complexes of the triamine type as a function of their composition and structure. Izv Akad Nauk Ser Biol. May-Jun. 1995;(3):281-90. English abstract found on p. 290.
Jamieson et al., Structure, Recognition, and Processing of Cisplatin-DNA Adducts. Chem Rev. 1999;99:2467-98.
Jin et al., Platinum(II) triammine antitumour complexes: structure-activity relationship with guanosine 5'-monophosphate (5'-GMP). Inorganica Chimica Acta. 2005;358:677-86.
Jung et al., RNA polymerase II blockage by cisplatin-damaged DNA. Stability and polyubiquitylation of stalled polymerase. J Biol Chem. Jan. 20, 2006;281(3):1361-70. Epub Nov. 7, 2005.
Kapp et al., Dinuclear alkylamine platinum(II) complexes of [1,2-bis(4-fluorophenyl)ethylenediamine]platinum(II): influence of endocytosis and copper and organic cation transport systems on cellular uptake. ChemMedChem. May 2006;1(5):560-4.
Kartalou et al., Mechanisms of resistance to cisplatin. Mutat Res. Jul. 1, 2001;478(1-2):23-43.
Kawai et al., Synthesis, structure and antitumor activity of a new water-soluble platinum complex, (1R,2R-cyclohexanediamine-N,N')[2-hydroxy-4-oxo-2-pentenoato(2-)-O2] platinum(II). Chem Pharm Bull (Tokyo). Feb. 1993;41(2):357-61.
Keck et al., Unwinding of supercoiled DNA by platinum-ethidium and related complexes. J Am Chem Soc. 1992;114:3386-90.
Kelland et al., The resurgence of platinum-based cancer chemotherapy. Nat Rev Cancer. Aug. 2007;7(8):573-84. Epub Jul. 12, 2007.
Kidani et al., Antitumor activity of 1,2-diaminocyclohexane—platinum complexes against sarcoma-180 ascites form. J Med Chem. Dec. 1978;21(12):1315-8.
Kostova, Platinum complexes as anticancer agents. Recent Pat Anticancer Drug Discov. Jan. 2006;1(1):1-22.
Lebwohl et al., Clinical development of platinum complexes in cancer therapy: an historical perspective and an update. Eur J Cancer. Sep. 1998;34(10):1522-34.
Lee et al., Transcription-coupled and DNA damage-dependent ubiquitination of RNA polymerase II in vitro. Proc Natl Acad Sci U S A. Apr. 2, 2002;99(7):4239-44. Epub Mar. 19, 2002.
Lempers et al., The new antitumor compound, cis-[Pt(NH3)2(4-methylpyridine)Cl]Cl, does not form N7,N7-d(GpG) chelates with DNA. An unexpected preference for platinum binding at the 5'G in d(GpG). J Inorg Biochem. Sep. 1990;40(1):23-35.
Lippard , Chemical synthesis: the art of chemistry. Nature. Apr. 11, 2002;416(6881):587.
Lovejoy et al., cis-Diammine(pyridine)chloroplatinum(II), a monofunctional platinum(II) antitumor agent: Uptake, structure, function, and prospects. Proc Natl Acad Sci U S A. Jul. 1, 2008;105(26):8902-7. doi: 10.1073/pnas.0803441105. Epub Jun. 25, 2008.
Lovejoy et al., Non-traditional platinum compounds for improved accumulation, oral bioavailability, and tumor targeting. Dalton Trans. Dec. 28, 2009;(48):10651-9. doi: 10.1039/b913896j. Epub Oct. 1, 2009.
Lovejoy et al., Spectrum of cellular responses to pyriplatin, a monofunctional cationic antineoplastic platinum(II) compound, in human cancer cells. Mol Cancer Ther. Sep. 2011;10(9):1709-19. doi: 10.1158/1535-7163.MCT-11-0250. Epub Jul. 12, 2011.

(56) References Cited

OTHER PUBLICATIONS

Margiotta et al., Sterically hindered complexes of platinum(II) with planar heterocyclic nitrogen donors. A novel complex with 1-methylcytosine has a spectrum of activity different from cisplatin and is able of overcoming acquired cisplatin resistance. J Inorg Biochem. Nov. 2006;100(11):1849-57. Epub Aug. 3, 2006.
Martin et al., Do structurally similar molecules have similar biological activity? J Med Chem. Sep. 12, 2002;45(19):4350-8.
Misset et al., Oxaliplatin clinical activity: a review. Crit Rev Oncol Hematol. Aug. 2000;35(2):75-93.
Mukhopadhyay et al., Conjugated platinum(IV)—peptide complexes for targeting angiogenic tumor vasculature. Bioconjug Chem. Jan. 2008;19(1):39-49. Epub Sep. 11, 2007.
Muscella et al., [Pt(O,O'-acac)(gamma-acac)(DMS)], a new Pt compound exerting fast cytotoxicity in MCF-7 breast cancer cells via the mitochondrial apoptotic pathway. Br J Pharmacol. Jan. 2008;153(1):34-49. Epub Nov. 19, 2007.
Muscella et al., New platinum(II) complexes containing both an O,O'-chelated acetylacetonate ligand and a sulfur ligand in the platinum coordination sphere induce apoptosis in HeLa cervical carcinoma cells. Biochem Pharmacol. Jun. 30, 2007;74(1):28-40. Epub Mar. 31, 2007.
Muscella et al., Sublethal concentrations of the platinum(II) complex [Pt(O,O'-acac)(gamma-acac)(DMS)] alter the motility and induce anoikis in MCF-7 cells. Br J Pharmacol. Jul. 2010;160(6):1362-77. doi: 10.1111/j.1476-5381.2010.00782.x.
Osol [Editor]. "Chapter 27: Structure-Activity Relationship and Drug Design". Remington's Pharmaceutical Sciences (Sixteenth Edition). Mack Publishing. 1980. pp. 420-435.
Page et al., Effect of the diaminocyclohexane carrier ligand on platinum adduct formation, repair, and lethality. Biochemistry. Jan. 30, 1990;29(4):1016-24.
Park et al., Phenanthriplatin, a monofunctional DNA-binding platinum anticancer drug candidate with unusual potency and cellular activity profile. Proc Natl Acad Sci U S A. Jul. 24, 2012;109(30):11987-92. doi: 10.1073/pnas.1207670109. Epub Jul. 6, 2012.
Peer et al., Nanocarriers as an emerging platform for cancer therapy. Nat Nanotechnol. Dec. 2007;2(12):751-60. doi: 10.1038/nnano.2007.387.
Pérez et al., Current status of the development of trans-platinum antitumor drugs. Crit Rev Oncol Hematol. Aug. 2000;35(2):109-20.
Pinto et al., Binding of the antitumor drug cis-diamminedichloroplatinum(II) (cisplatin) to DNA. Biochim Biophys Acta. 1985;780(3):167-80.
Portney et al., Nano-oncology: drug delivery, imaging, and sensing. Anal Bioanal Chem. Feb. 2006;384(3):620-30. Epub Jan. 27, 2006.
Reardon et al., Efficient nucleotide excision repair of cisplatin, oxaliplatin, and Bis-aceto-ammine-dichloro-cyclohexylamine-platinum(IV) (JM216) platinum intrastrand DNA diadducts. Cancer Res. Aug. 15, 1999;59(16):3968-71.
Reardon et al., Purification and characterization of *Escherichia coli* and human nucleotide excision repair enzyme systems. Methods Enzymol. 2006;408:189-213.
Sakai et al., A New One-Dimensional Platinum System Consisting of Carboxylate-Bridged cis-Diammineplatinum Dimers1. JACS. 1998;120:11353-63.
Schwartz et al., Preparation and antitumor evaluation of water-soluble derivatives of dichloro(1,2-diaminocyclohexane)platinum(II). Cancer Treat Rep. Nov. 1977;61(8):1519-25.
Silverman et al., 2.4-A crystal structure of the asymmetric platinum complex [Pt(ammine)(cyclohexylamine)]2+ bound to a dodecamer DNA duplex. J Biol Chem. Dec. 20, 2002;277(51):49743-9. Epub Oct. 10, 2002.
Spingler et al., 2.4 A crystal structure of an oxaliplatin 1,2-d(GpG) intrastrand cross-link in a DNA dodecamer duplex. Inorg Chem. Oct. 22, 2001;40(22):5596-602.
Sporn et al., Chemoprevention of cancer. Carcinogenesis. Mar. 2000;21(3):525-30.
Stephen et al., The structural characterisation and elucidation of the electronic structure of the mononuclear Pt(III) complex [Pt([9]aneS3)2]3+ ([9]aneS3 = 1,4,7-trithiacyclononane). Chem Commun (Camb). Nov. 30, 2008;(44):5707-9. doi: 10.1039/b811645h. Epub Sep. 30, 2008.
Takahara et al., Crystal structure of the anticancer drug cisplatin bound to duplex DNA. J Am Chem Soc. 1996;118:12309-21.
Thoppil et al., Terpenoids as potential chemopreventive and therapeutic agents in liver cancer. World J Hepatol. Sep. 27, 2011;3(9):228-49. doi: 10.4254/wjh.v3.i9.228.
Todd et al., Inhibition of transcription by platinum antitumor compounds. Metallomics. 2009;1(4):280-91. doi: 10.1039/b907567d.
Trafton, MIT researchers see alternative to common colorectal cancer drug. News Office. Jun. 17, 2008. Last accessed Jun. 23, 2008. 2 pages.
Wang et al., Cellular processing of platinum anticancer drugs. Nat Rev Drug Discov. Apr. 2005;4(4):307-20.
Wang et al., X-ray structure and mechanism of RNA polymerase II stalled at an antineoplastic monofunctional platinum-DNA adduct. Proc Natl Acad Sci U S A. May 25, 2010;107(21):9584-9. doi: 10.1073/pnas.1002565107. Epub May 6, 2010.
Weiss et al., New cisplatin analogues in development. A review. Drugs. Sep. 1993;46(3):360-77.
Whittaker et al., The interaction of DNA-targeted platinum phenanthridinium complexes with DNA. Nucleic Acids Res. Sep. 1, 1998;26(17):3933-9.
Wilson et al., Acetate-bridged platinum(III) complexes derived from cisplatin. Inorg Chem. Sep. 17, 2012;51(18):9852-64. doi: 10.1021/ic301289j. Epub Sep. 4, 2012.
Wilson et al., In vitro anticancer activity of cis-diammineplatinum(II) complexes with β-diketonate leaving group ligands. J Med Chem. Jun. 14, 2012;55(11):5326-36. doi: 10.1021/jm3002857. Epub May 18, 2012.
Wilson et al., Synthesis, characterization, and cytotoxicity of platinum(IV) carbamate complexes. Inorg Chem. Apr. 4, 2011;50(7):3103-15. doi: 10.1021/ic2000816. Epub Mar. 1, 2011.
Wilson, New Constructs for Platinum Anticancer Prodrugs. Presentation. Oct. 19, 2011. 41 pages.
Wong et al., Current status of platinum-based antitumor drugs. Chem Rev. Sep. 8, 1999;99(9):2451-66.
Yalçin, Studies on cis-DDP, [Pt(Dach)(MePhSO)Cl]+ and [PtNH3)2(N-Py)Cl]+ binding to fumarase. Drug Metabol Drug Interact. 1995;12(2):105-15.
Yonezawa et al., Cisplatin and oxaliplatin, but not carboplatin and nedaplatin, are substrates for human organic cation transporters (SLC22A1-3 and multidrug and toxin extrusion family). J Pharmacol Exp Ther. Nov. 2006;319(2):879-86. Epub Aug. 16, 2006.
Zamble et al., Cisplatin and DNA repair in cancer chemotherapy. Trends Biochem Sci. Oct. 1995;20(10):435-9.
Zamble et al., Repair of cisplatin—DNA adducts by the mammalian excision nuclease. Biochemistry. Aug. 6, 1996;35(31):10004-13.
Zhang et al., Organic cation transporters are determinants of oxaliplatin cytotoxicity. Cancer Res. Sep. 1, 2006;66(17):8847-57.
Zhu et al., Monofunctional platinum-DNA adducts are strong inhibitors of transcription and substrates for nucleotide excision repair in live mammalian cells. Cancer Res. Feb. 1, 2012;72(3):790-800. doi: 10.1158/0008-5472.CAN-11-3151. Epub Dec. 16, 2011.
Zorbas-Seifried et al., Reversion of structure-activity relationships of antitumor platinum complexes by acetoxime but not hydroxylamine ligands. Mol Pharmacol. Jan. 2007;71(1):357-65.
Abramkin et al., Solid-phase synthesis of oxaliplatin-TAT peptide bioconjugates. Dalton Trans. Mar. 14, 2012;41(10):3001-5. doi: 10.1039/c2dt12024k. Epub Jan. 27, 2012.
Barragan et al., Solid-phase synthesis and DNA binding studies of dichloroplatinum(ii) conjugates of dicarba analogues of octreotide as new anticancer drugs. Chem Commun (Camb). Aug. 21, 2009;(31):4705-7. doi: 10.1039/b909698a. Epub Jun. 22, 2009.
Barragan et al., Somatostatin subtype-2 receptor-targeted metal-based anticancer complexes. Bioconjug Chem. Sep. 19, 2012;23(9):1838-55. Epub Aug. 20, 2012.

(56) References Cited

OTHER PUBLICATIONS

Borrelli et al., A molecular carrier to transport and deliver cisplatin into endometrial cancer cells. Chem Biol Drug Des. Jul. 2012;80(1):9-16. doi: 10.1111/j.1747-0285.2012.01337.x. Epub Apr. 27, 2012.

Cullen et al., Mitochondria as a critical target of the chemotheraputic agent cisplatin in head and neck cancer. J Bioenerg Biomembr. Feb. 2007;39(1):43-50.

Damian et al., Synthesis and DNA Interaction of Platinum Complex/Peptide Chimera as Potential Drug Candidates. Eur J Org Chem. Nov. 2010; 2010(32): 6161-70.

Dodd et al., Peptide nucleic acid Pt(II) conjugates: a preliminary study of antisense effects in Xenopus laevis. Nucleosides Nucleotides Nucleic Acids. Apr. 2011;30(4):257-63. doi: 10.1080/15257770.2011.580290.

Galanski et al., Update of the preclinical situation of anticancer platinum complexes: novel design strategies and innovative analytical approaches. Curr Med Chem. 2005;12(18):2075-94.

Gaviglio et al., Synthesis and in vitro cytotoxicity of cis,cis,trans-diamminedichloridodisuccinatoplatinum(IV)-peptide bioconjugates. Metallomics. Mar. 2012;4(3):260-6. doi: 10.1039/c2mt00171c. Epub Feb. 7, 2012.

Hall et al. Platinum(IV) antitumour compounds: their bioinorganic chemistry. Coord Chem Rev. 2002; 232:49-67.

Ndinguri et al., Peptide targeting of platinum anti-cancer drugs. Bioconjug Chem. Oct. 21, 2009;20(10):1869-78. doi: 10.1021/bc900065r. Epub Sep. 23, 2009.

Rabik et al., Molecular mechanisms of resistance and toxicity associated with platinating agents. Cancer Treat Rev. Feb. 2007;33(1):9-23. Epub Nov. 3, 2006.

Robillard et al. Solid-phase synthesis of peptide-platinum complexes using platinum-chelating building blocks derived from amino acids. New J Chem. 2005. 29: 220-5.

Robillard et al., Automated parallel solid-phase synthesis and anticancer screening of a library of peptide-tethered platinum(II) complexes. J Comb Chem. Nov.-Dec. 2003;5(6):821-5.

Robillard et al., The First Solid-Phase Synthesis of a Peptide-Tethered Platinum(II) Complex. Angew Chem Int Ed Engl. Sep. 1, 2000;39(17):3096-3099.

Robillard et al., The interaction of peptide-tethered platinum(II) complexes with DNA. J Inorg Biochem. Aug. 1, 2003;96(2-3):331-8.

Siddik, Cisplatin: mode of cytotoxic action and molecular basis of resistance. Oncogene. Oct. 20, 2003;22(47):7265-79.

Suntharalingam et al., Conjugation of vitamin E analog α-TOS to Pt(IV) complexes for dual-targeting anticancer therapy. Chem Commun (Camb). Mar. 7, 2014;50(19):2465-8. doi: 10.1039/c3cc48740g. Epub Jan. 23, 2014.

Van Zutphen et al., Combinatorial discovery of new asymmetric cis platinum anticancer complexes is made possible with solid-phase synthetic methods. J Inorg Biochem. Oct. 2005;99(10):2032-8.

Van Zutphen et al., Extending solid-phase methods in inorganic synthesis: the first dinuclear platinum complex synthesised via the solid phase. Chem Commun (Camb). Mar. 7, 2003;(5):634-5.

Wong et al., Harnessing chemoselective imine ligation for tethering bioactive molecules to platinum(IV) prodrugs. Dalton Trans. May 28, 2012;41(20):6104-11. doi: 10.1039/c2dt30264k. Epub Mar. 16, 2012.

Wisnovsky et al., Targeting mitochondrial DNA with a platinum-based anticancer agent. Chem Biol. Nov. 21, 2013;20(11):1323-8. doi: 10.1016/j.chembiol.2013.08.010. Epub Oct. 31, 2013.

Deng et al., Crystallographic characterization of trans-bis(acetato)(1,1-cyclobutanedicarboxylato)ethylenediamineplatinum(IV) trihydrate. Inorganica Chimica Acta. Feb. 1, 1993;204(1):35-38.

Mi et al., Vitamin E TPGS prodrug micelles for hydrophilic drug delivery with neuroprotective effects. Int J Pharm. Nov. 15, 2012;438(1-2):98-106. doi: 10.1016/j.ijpharm.2012.08.038. Epub Aug. 29, 2012.

* cited by examiner

PLATINUM (IV) COMPLEXES FOR USE IN DUAL MODE PHARMACEUTICAL THERAPY

RELATED APPLICATIONS

This application is a national-stage application under 35 U.S.C. §371 of International Patent Application No. PCT/US2009/004846, filed Aug. 26, 2009, entitled "Platinum (IV) Complexes For Use In Dual Mode Pharmaceutical Therapy," by Lippard, et al., which claims priority to U.S. Provisional Patent Application Ser. No. 61/091,977, filed Aug. 26, 2008, entitled "Mitochondria Targeting Platinum (IV) Complexes with Dual Cell Killing Modes," by Lippard, et al., and U.S. Provisional Patent Application Ser. No. 61/196,419, filed Oct. 17, 2008, entitled "Dual Mode Pharmaceutical Therapy," by Dhar, et al., each of which is incorporated herein by reference.

STATEMENT REGARDING FEDERALLY SPONSORED RESEARCH OR DEVELOPMENT

This invention was made with government support under Grant No. 5-R37-CA034992-26, awarded by the National Institute of Health. The government has certain rights in this invention.

FIELD OF THE INVENTION

The present invention relates to compositions, kits, and methods for treatment of cancers using compositions comprising at least a first component comprising a precursor of a therapeutically active platinum agent and a second component comprising a precursor of a second therapeutically active agent.

BACKGROUND OF THE INVENTION

Platinum drugs are widely used in cancer therapy. Among the platinum drugs, cisplatin, carboplatin, and oxaliplatin have FDA approval and are clinically used in the United States and elsewhere. The use of platinum(II) drugs in the treatment of malignancies has been somewhat limited because of the side effects and resistance acquired by cancer cells. An alternative to platinum(II) drug candidates is the use of substitutionally more inert platinum(IV) compounds as prodrugs derived from clinically effective platinum(II) compounds. Substitutionally inert platinum(IV) complexes are less likely to be deactivated prior to reaching their destination target in the cancer cell. The activity of platinum(IV) complexes generally involves reduction with concomitant loss of the axial ligands, affording an active platinum(II) complex that readily binds to DNA. The axial ligands which are released from the platinum(IV) complex may comprise a therapeutically active agent.

It is known that cancer cells may have cellular pathways that differ from non-cancerous cells, which may be targeted by anticancer therapies. For example, it has been recently recognized that mitochondrion may be a target for anticancer therapy due to its role in arbitrating cell apoptosis.

Therefore, it would be beneficial to have methods and compositions for treating cancer using a dual mode therapy comprising a platinum drug and an agent which specifically affects a cellular pathway of a cancer cell.

SUMMARY OF THE INVENTION

The present invention relates to compositions, kits, and methods for treatment of cancers using compositions comprising at least a first component comprising a precursor of a therapeutically active platinum agent and a second component comprising a precursor of a second therapeutically active agent. The subject matter of the present invention involves, in some cases, interrelated products, alternative solutions to a particular problem, and/or a plurality of different uses of one or more systems and/or articles.

In one aspect, the invention is directed towards a composition. According to a first embodiment, a composition of matter comprises a compound having the formula,

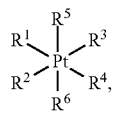

Wherein $R^1$, $R^2$, $R^3$, and $R^4$ can be the same or different and each is a group comprising at least one of ammonia, an amine, an aryl group, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted; and $R^5$ and $R^6$ can be the same or different and at least one acts as a therapeutically active compound, or a precursor of a therapeutically active compound, when dissociated from platinum, wherein the therapeutically active compound selectively affects a cellular pathway of a cancer cell and is substantially inactive toward non-cancerous cells.

According to another embodiment, a composition of matter comprises a compound having the formula,

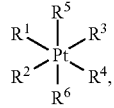

wherein $R^1$ and $R^2$ can be the same or different and each is a group comprising at least one of ammonia, an amine, an aryl group, or a heterocycle including at least one nitrogen, any being optionally substituted, or, $R^1$ and $R^2$ can be joined together to form a bidentate ligand, any being optionally substituted; and $R^3$, $R^4$, $R^5$, and $R^6$ can be the same or different and at least one acts as a therapeutically active compound, or a precursor of a therapeutically active compound, when dissociated from platinum, wherein the therapeutically active compound selectively affects a cellular pathway of a cancer cell and is substantially inactive toward non-cancerous cells.

In another aspect, the invention provides a method of treating a patient in need of a therapeutic protocol. According to one embodiment, a method of treating a patient in need of a therapeutic protocol comprises administering to the patient a composition comprising at least a first component comprising a precursor of a therapeutically active platinum agent and a second component comprising a precursor of a second therapeutically active agent, wherein, upon uptake of the composition into a cell, the first component and the second component dissociate from each other to form a first therapeutically active platinum agent or a second generation precursor to a therapeutically active agent and a second therapeutically active agent or a second generation precursor to a therapeutically active agent, wherein the second therapeutically active agent targets a specific cellular pathway of a cancer cell and is substantially inactive toward non-cancerous cells.

Figure 1:
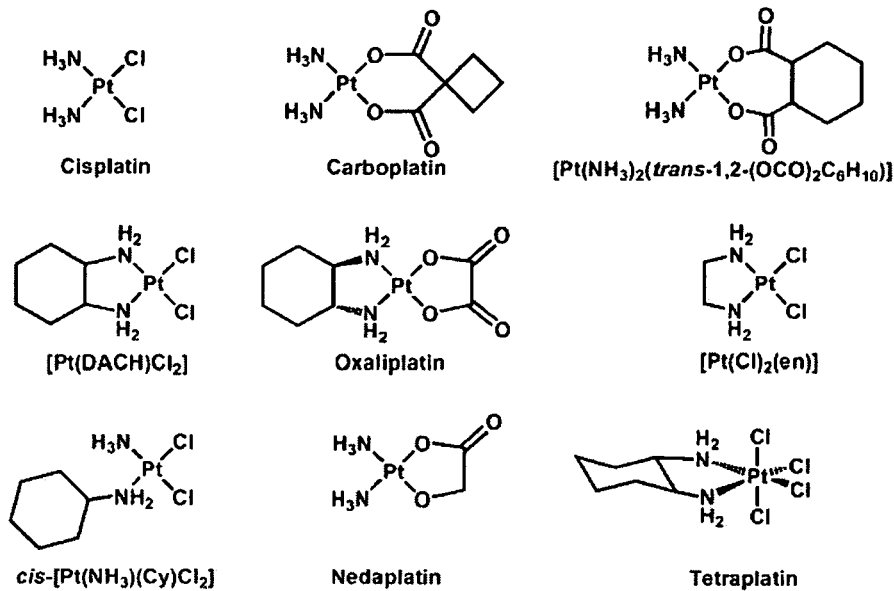
FIG. 1 shows examples of therapeutically active platinum (II) agents.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The invention provides compositions, preparations, formulations, kits, and methods useful for treating subjects having cancer or at risk of developing cancer. The subject matter of the present invention involves, in some cases, interrelated products, alternative solutions to a particular problem, and/or a plurality of different uses of one or more systems and/or articles.

More specifically, in one set of embodiments, the present invention provides methods and compositions for treating cancer or other physiological conditions via a dual mode therapy. The dual mode therapy can involve administering to a patient a composition comprising a precursor to a therapeutically active platinum agent and a precursor to a second therapeutically active agent. Following administration, a therapeutically active platinum agent or a second generation precursor to a therapeutically active platinum agent and a second therapeutically active agent or a second generation precursor to a second therapeutically active agent may form, where the second therapeutically active agent specifically affects a cellular pathway of cancer cells and may be largely inactive with respect to cellular pathways of non-cancerous cells. The methods and compositions of the present invention which employ dual mode therapies may be beneficial over the therapies used alone. For example, the treatment of a cancer with a dual mode therapy of the present invention may be more effective than treatment of the cancer with a therapeutically active platinum agent alone, as described full below.

Compositions of the invention can include a precursor to a therapeutically active agent that affects a cellular pathway of a cancer cell. "Precursor," as used herein, means a composition which, after undergoing loss and/or gain of a ligand, functional group, or the like, and/or undergoing a reaction (e.g., chemical reaction of a functional group), dissociation from a mixture, etc., is a therapeutically active agent effective at treating a subject indicted for treatment for cancer (a subject at risk of, or currently or previously afflicted with cancer). It should be understood, however, that in some embodiments, a precursor to a therapeutically active agent may form a second generation precursor to a therapeutically active agent. The second generation precursor may undergo transformation to form the therapeutically active agent, or, in some cases, a third generation precursor.

In some embodiments, the therapeutically active agent may affect a cellular pathway of a cancer cell and lead to cell death or apoptosis. The therapeutically active agent typically (but not in all cases) does not substantially affect non-cancerous cells, i.e., when the agent is exposed to non-cancerous cells in non-trace amounts, it does not affect the cellular pathway significantly. That is, the therapeutically active agent may have deleterious affects on the cancer cells (e.g., causing death of the cells) and/or affect cancer cells to a higher degree (e.g., ten-fold, 50-fold, 100-fold, 1000-fold) than non-cancerous cells.

It is to be understood that the specific compositions disclosed or exemplified herein are for purposes of illustration only, and other compositions can be used so long as they meet the requirements of the claimed invention. Those of ordinary skill in the art of chemical therapeutics can readily select first and second components, as described functionally herein, bound to each other in a way such that they can be delivered together to a treatment site, and partially or fully dissociate from each other to form a first therapeutically active agent (or second generation precursor) and a second therapeutically active agent (or second generation precursor), the second therapeutically active agent being an agent which targets a specific cellular pathway of a cancer cell and is substantially inactive toward non-cancerous cells.

In some embodiments, the present invention is directed towards compositions comprising at least a first component comprising a precursor of a therapeutically active platinum agent and a second component comprising a precursor of a second therapeutically active agent. In some embodiments, upon uptake of the composition into a cell, the first component and the second component dissociate from each other to form a platinum(II) therapeutically active agent or a second generation precursor to a platinum(II) therapeutically active agent and a second therapeutically active agent or a second generation precursor to a second therapeutically active agent (the second therapeutically active agent being an agent, as described above, that selectively affects a cellular pathway of a cancer cell and may be substantially inactive toward non-cancerous cells). It is to be understood that where platinum agents are discussed at any point herein, other agents as described herein can be used, and the specific embodiment disclosed is not limited to platinum agents.

The precursor to the second therapeutically active agent can be bound to the precursor to the first therapeutically active (e.g., platinum) agent in any of a number of ways including covalent bonding, ionic bonding, coordinative coupling, or the like. Typically, the second therapeutically active agent is covalently bound to the first therapeutically active agent. In certain embodiments, release of the precursor to the second therapeutically active agent from the platinum center of the precursor to the therapeutically active platinum agent may be precipitated by a redox change of the platinum center. For example, the precursor to the therapeutically active platinum agent may comprise a platinum(IV) center which may be reduced to a platinum(II) center, as described herein. In certain instances, the redox change may cause the precursor to the second therapeutically active agent to be released from the platinum center, whereas in other instances, the redox change could make it more likely that the precursor to the second therapeutically active agent is subsequently released from the platinum. For example, a redox change of platinum may directly cause the precursor to the second therapeutically active agent to dissociate from the platinum center immediately. An example of such an instance is a redox change that causes a change in coordination geometry for the platinum center that reduces the number of ligands, thereby causing the precursor to the second therapeutically active agent to dissociate and thus be released. Alternatively, such a redox change may increase the likelihood that the precursor to the second therapeutically active agent disassociates over time or is displaced by another ligand. For example, a redox change could make substitution at the platinum center more likely whereas before the redox change substitution was not as likely. In addition and without limitation, for all of the subject coordination complexes, it may be the case that a covalently attached precursor to a second therapeutically active agent is released over time after administration without any redox change at the metal center, notwithstanding whether a redox changes causes or increases the likelihood of release of the precursor to the therapeutically active agent.

The platinum(IV) composition may be more likely to undergo a redox change following uptake into a cell. That is, the reducing environment of a cell may enhance the ability of the agent to be reduced from a platinum(IV) precursor to a platinum(II) therapeutically active agent. For example, a therapeutically active platinum(IV) precursor composition may not be reduced to form a therapeutically active platinum (II) composition prior to inclusion within a cell. That is, the reducing environment within cells may facilitate or enhance a redox change at the platinum center, precipitating release of the precursor to the second therapeutically active agent. By this mechanism, for certain subject coordination complexes, release of a covalently attached therapeutically active agent precursor can occur (or be more likely to occur) in the cell upon reduction of the metal ion to which the therapeutically active agent precursor is covalently attached. By this means, the platinum(II) therapeutically active agent and the second therapeutically active agent may be generated in the same cell simultaneously. It may be the case that the therapeutically active platinum agent and the second therapeutically active agents may act synergistically or independently. For example and without limitation, as described herein, the second therapeutically active agent may affect a specific cellular pathway of a cancer cell and may not substantially affect cellular pathways of non-cancerous cells. In some embodiments, the composition may be substantially therapeutically inactive prior to uptake into a cell (e.g., the composition has substantially no therapeutic activity prior to uptake into a cell, i.e., prior to reduction within the cell).

In one aspect, the present invention relates to methods for treating a patient, such as a patient indicated for treatment for cancer. According to the first set of embodiments, a method comprises administering to a patient a composition comprising at least a first component comprising a precursor of a therapeutically active platinum agent and a second component comprising a precursor of a second therapeutically active agent. In some embodiments, upon uptake of the composition into a cell, the first component and the second component dissociate from each other to form a first therapeutically active platinum agent (or a second generation precursor to a therapeutically active platinum agent) and a second therapeutically active agent (or a second generation precursor to a second therapeutically active agent), wherein the second therapeutically active agent affects a specific cellular pathway of a cancer cell. In some embodiments, the $IC_{50}$ value of a composition of the present invention comprising a precursor of a therapeutically active platinum agent and a precursor to a second therapeutically active agent may be at least about 1%, at least about 2%, at least about 5%, at least about 10%, at least about 15%, at least about 20%, at least about 30%, at least about 40%, at least about 50%, at least about 60%, at least about 70%, at least about 100%, or more, greater than the $IC_{50}$ value of the therapeutically active platinum agent alone, when administered in a substantially similar manner.

In some embodiments, a first component of a composition comprises a platinum(IV) complex which is a precursor to a therapeutically active platinum agent (or a second generation precursor to therapeutically active platinum agent), while a second component comprises a precursor to a second therapeutically active agent (or a second generation precursor to a second therapeutically active agent), wherein the therapeutically active agent is capable of targeting a specific cellular pathway of a cancer cell and does not substantially affect non-cancerous cells. For example, exposure of a plurality of cancer cells and a plurality of non-cancerous cells to the therapeutically active agent may substantially affect the plurality of cancer cells (e.g., cause the cancer cells to die or leads to the cell death) and may not substantially affect the non-cancerous cells (e.g., may not cause the non-cancerous cells to die or may not lead to cell death). In some cases, a therapeutically active agent may be determined to substantially affect cancer cells and have no substantial effect on non-cancerous cells (e.g., the agent is substantially inactive towards non-cancerous cells) by determining the ratio of cancer cells which are affected (e.g., resulting in cell death by the agent) to non-cancerous cells which are affected, following exposure to the therapeutically active agent. For example, the ratio of cancer cells to non-cancerous cells which are affected (e.g., cell death) upon exposure to a therapeutically active agent is at least about 10:1, at least about 100:1, at least about 500:1, at least about 1000:1, at least about 5000:1, at least about 10,000:1, at least about 100,000:1, or greater. Those of ordinary skill in the art would be aware of methods and technologies for determining the ratio of cancerous cells to non-cancerous cells affected by the agent, as well as the number of cells which undergo cell death upon exposure to the agent. Other parameters may also be determined when determining whether an agent affects a cancer cell and/or a non-cancerous cell, for example, tumor size, membrane potential of a cell, or presence or absence of a compound in parts of the cell (e.g., cytochrome c, apoptosis inducing factor, etc.).

In some cases, the second therapeutically active agent may be a small molecule. The term "small molecule" is art-recognized and refers to a composition which has a molecular weight of less than about 2000 g/mole, or less than about 1000 g/mole, and even less than about 500 g/mole. Small molecules may include, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides, or polypeptides.

In some embodiments, the therapeutically active agent may target the mitocondria of a cancer cell. The mitocondria may be a suitable target for the therapeutically active agent as the mitochondria may be involved in controlling cell apoptosis. In some cases, an agent may be selected to target the mitochondria of cancer cells and may have limited or no adverse affects on non-cancerous cells (e.g., is substantially non-toxic).

In a certain embodiment, the therapeutically active agent may comprise dichloroacetic acid (DCA) which has been shown to attack the mitochondria of cancer cells and cause the cells to commit cellular suicide or cause apoptosis. DCA has not been found to adversely affect non-cancerous cells. In some instances, DCA may have deleterious effects on cancer cells by affecting the metabolism of the mitochondria. For example, a dichloroacetate ion may stimulate the activity of the mitochondrial enzyme pyruvate dehydrogenase (PDH) by inhibiting the enzyme pyruvate dehydrogenase kinase (PDK). DCA may shift the metabolism from glycolysis to glucose oxidation, which decreases the mitochondrial membrane potential. This activity may open mitochondrial transition pores and allow for the translocation of proapoptotic mediators like cytochrome c and apoptosis inducing factor (AIF), leading to apoptosis.

In some embodiments, the therapeutically active agent may comprise targeted cancer therapies, as will be known to those or ordinary skill in the art. As described herein, in some cases, the therapeutically active agent may comprise a small molecule, or more specifically, a small molecule drug. In some cases, small molecule drugs may function by blocking specific enzymes involved in cancer cell growth and may be also referred to as signal-transduction inhibitors. Non-limiting examples of small molecule drugs include Gleevec® (e.g., imatinib mesylate) which is a tyrosine kinase inhibitor, and Iressa® (e.g., gefitinib) which targets the epidermal growth factor receptor which is overproduced by many types of cancer cells (e.g., tyrosine kinase domain).

In some cases, the therapeutically active agent may be an apoptosis-inducing drug and cause a cancer cell to undergo apoptosis by interfering with proteins involved in the process. Non-limiting examples of therapeutically active agents which may be apoptosis-inducing include Velcade® (e.g., bortezomib) which is a proteasome inhibitor, and Genasense™ (e.g., oblimersen) which blocks the production of BCL-2 which promotes the survival of tumor cells. Other non-limiting examples of therapeutically active agents a composition may comprise include HDAC inhibitors (e.g., histone deacetylase inhibitors such as suberoylanilide hydroxamic acid, SAHA), Hsp90 inhibitors (e.g., XL888 (Exelixis, Inc), 17-Allylamino-17-demethoxygeldanamycin (17-AAG)), aurora inhibitors (e.g., AT9283 (Astex Therapeutics)), cyclin-dependent kinase inhibitors (e.g., Flavopiridol (e.g., Alvocidib™), olomoucine, roscovitine, puvalanol B, dihydroindolo(3,2-d)(1)benzazepinone kenpaullone, indirubin-3-monoxime, diaminothiazoles (e.g., AG12275)), and α-Tocopherol compounds (e.g., comprising lysine, succinic, butyric acid, etc.). Hsp90 client proteins include mutated p53, Bcr/Abl, Raf-1, Akt, HER2/Neu (ErbB2), and HIF-1α. In some embodiments, the therapeutically active agent is not a steroid.

In some aspects, the present inventions relates to compositions. According to a first set of embodiments, a composition of matter comprises a compound having the formula,

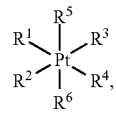

wherein, $R^1$, $R^2$, $R^3$, and $R^4$ can be the same or different and each is a group comprising at least one of ammonia, an amine, an aryl group, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted, and $R^5$ and $R^6$ can be the same or different and at least one acts as a therapeutically active compound, or a precursor of a therapeutically active compound, when dissociated from platinum, wherein the therapeutically active compound selectively affects a cellular pathway of a cancer cell and is substantially inactive toward non-cancerous cells.

In some embodiments, at least two of $R^1$, $R^2$, $R^3$, $R^4$, $R^5$ and $R^6$ are selected such that, upon exposure to a cellular environment, a therapeutically active platinum compound forms or a second generation precursor to a therapeutically active platinum compound forms. For example, $R^1$ and $R^2$ may be essential groups for the formation of a therapeutically active platinum agent (e.g., groups which are required for a platinum compound to be therapeutically active compound, wherein $R^3$-$R^6$ may be any variety of ligands and/or optionally absent). In some cases, $R^3$, $R^4$, $R^5$, and $R^6$ may be the same or different and each may be a leaving groups or a precursor to a second therapeutically active compound. In some embodiments, upon exposure to a cellular environment, $R^3$, $R^4$, $R^5$, and $R^6$ may dissociate from the platinum center, and at least two new ligands may associate with the platinum center (e.g., $R^7$ and $R^8$, as shown in Equation 1) to form a therapeutically active platinum compound (e.g., $[Pt(R^1)(R^2)(R^7)(R^8)]$).

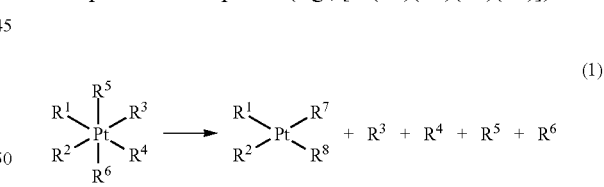

(1)

$R^7$ and $R^8$ may be the same or different and may be any suitable ligand as will be known to those of ordinary skill in the art, and are generally ligands or groups present in the environment surrounding the compound during dissociation of $R^3$, $R^4$, $R^5$ and/or $R^6$ (e.g., present in situ and/or in a cellular environment) and are capable of binding to platinum (e.g., water). It should be understood, that in some cases, less than all of $R^3$, $R^4$, $R^5$, and $R^6$ may dissociate from the platinum center and less than two ligands may associate with the platinum center. For example, $R^3$, $R^5$, and $R^6$ may dissociate from the platinum center and $R^8$ may associate, thereby forming a compound having the formula $[Pt(R^1)(R^2)(R^3)(R^8)]$. Those of ordinary skill in the art will be able to select appropriate combinations of ligands to form the desired therapeutically active complex. At least one of the ligands that dissociate may be selected such that it forms a second therapeutically active agent or a precursor to a therapeutically active agent.

In some cases, the at least two ligands are selected such that the ligands are cis to each other (e.g., $R^1$ and $R^2$, $R^1$ and $R^3$, $R^1$ and $R^5$, $R^1$ and $R^6$, $R^2$ and $R^4$, etc.). That is, the at least two ligands may not be trans to each other (e.g., $R^1$ and $R^4$, $R^2$ and $R^3$, $R^5$ and $R^6$). However, in some cases, the ligands may be selected such that they are trans to each other (e.g., in embodiments where the desired therapeutically active platinum agent has two essential ligands which are trans to each other). In some cases, the at least two ligands occupy equatorial positions of the compound. In some instances, however, one or more of the ligands may occupy an axial position of the compound. In some embodiments, more than two ligands may be essential for the formation of a therapeutically active platinum agent and those or ordinary skill in the art will be able to determine the required structure of the composition such that the essential ligands are present.

Accordingly, in some embodiments, at least two $R^1$, $R^2$, $R^3$, $R^4$, $R^5$ and $R^6$ may be the same or different and each is a group comprising at least one of ammonia, an amine, an aryl group, a heterocycle including at least one nitrogen, any being optionally substituted, or, the two ligands can be joined together to form a bidentate ligand, any being optionally substituted, and at least one of the other four ligands may comprise a compound which acts as a therapeutically active compound, or a second generation precursor to a therapeutically agent compound, when dissociated from platinum, wherein the therapeutically active compound selectively affects a cellular pathway of a cancer cell and is substantially inactive toward non-cancerous cells. The remaining ligands may be leaving groups.

As a specific example of the above, in some cases, $R^1$ and $R^2$ (e.g., two cis ligands) may be the same or different and each may be a group comprising at least one of ammonia, an amine, an aryl group, or a heterocycle including at least one nitrogen, any being optionally substituted, or, the two ligands may be joined together to form a bidentate ligand, any being optionally substituted, and $R^3$, $R^4$, $R^5$, and $R^6$ may be the same or different and at least one acts as a therapeutically active compound, or a precursor of a therapeutically active compound, when dissociated from platinum, wherein the therapeutically active compound selectively affects a cellular pathway of a cancer cell and is substantially inactive toward non-cancerous cells. In some instances, $R^3$, $R^4$, $R^5$ and/or $R^6$ comprise the same or different therapeutically active compound when dissociated form platinum.

In some embodiments, at least one of the $R^1$-$R^6$ is a second therapeutically active compound (or a second generation precursor to a second therapeutically active agent) which may affect a cellular pathway of a cancer cell (e.g., DCA, as described herein). In some cases, two, three, or four of the ligands are a second therapeutically active compound (or second generation precursor to a second therapeutically active agent) when dissociated from platinum. In some embodiments, those of $R^1$-$R^6$ which are not essentially ligand for the formation of a therapeutically active platinum agent and are not precursor to a therapeutically active agent, may be a leaving group, a non-interfering ligand, and/or a non-interfering group. As used herein, the term "non-interfering group," or "non-interfering ligand" refers to any group or ligand which does not significantly effect or alter the properties of the compound and, in some cases, does not affect or does not significantly affect a cellular pathway of a cancer cell.

In some embodiments, the compound may have the formula,

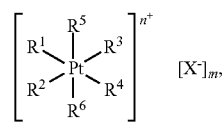

wherein, X is a counterion, and n and m are 1 or n and m are 2, and $R^1$-$R^6$ may be as described herein.

Non-limiting examples of compositions of the present invention include:

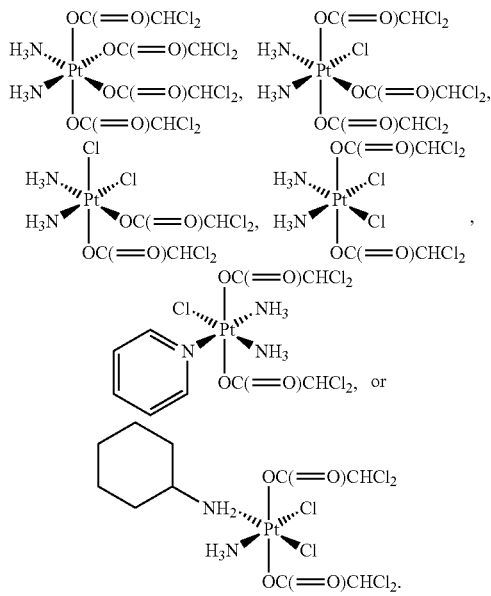

The leaving groups, non-interfering groups, and/or precursor to therapeutically active agents (e.g., in some cases, $R^5$ and $R^6$, in other cases, $R^3$, $R^4$, $R^5$, and $R^6$, etc.) may be covalently bound to the platinum center or may be associated with the platinum center via a tether. In some embodiments, at least one of these ligands (e.g., $R^3$, $R^4$, $R^5$ and/or $R^6$) may be released from the platinum(IV) center and a platinum (II) complex may form. In some cases, as discussed in more detail herein, the tether may comprise ester linkers that covalently link the second therapeutically active agent to the platinum center. The tether may be hydrolyzed, in some cases, by intracellular esterases and the second therapeutically active agent may be formed (e.g., dissociated from the platinum center and without coordination to a tether). In some cases, however, the second therapeutically active agent may be therapeutically active when it comprises the tether (e.g., when the tether remains associated with the second therapeutically active agent).

In some cases, at least two of the ligands (e.g., $R^3$, $R^4$, $R^5$, and/or $R^6$) may comprise the same or different precursor to a therapeutically active agent. For example, $R^5$ may comprise a precursor to a first therapeutically active agent and $R^6$ may comprise a precursor to a second therapeutically active agent. As another example, $R^5$ and $R^6$ may be different and $R^5$ (or $R^6$) may comprise a precursor to a therapeutically active agent and $R^6$ (or $R^5$) may comprise a non-therapeutically active agent.

In some embodiments, the precursor to a therapeutically active agent may be a small molecule, as described herein. In some cases, at least one of small molecule may have a molecular weight of less than about 800 g/mol, less than about 600 g/mole, less than about 400 g/mole, less than about 300 g/mole, less than about 200 g/mole, less than about 100 g/mole, or less. In a particular embodiment, the precursor to a therapeutically active agent does not comprise a steroid. In another embodiment, the precursor to a therapeutically active agent comprises the group, —OC(O)(CHCl$_2$) (e.g., DCA).

In some embodiments, the precursor to the second therapeutically active agent may either be directly attached (e.g., via a covalent bond) to the platinum center or attached to the platinum through a tether. When the therapeutic agent is not coordinated directly to the metal center, a variety of tethers can be used to link the therapeutic agent to the metal center. For example, the tether may be a hydrocarbon chain of various possible lengths containing at least one functional group which allows for release of the therapeutic agent under the right conditions. Non-limiting examples of functional groups which can be used in tethers include ester, amide, amine, and anhydride moieties.

In some embodiments, release of at least one ligand (e.g., $R^3$, $R^4$, $R^5$ and/or $R^6$, or in some cases, $R^5$ and $R^6$, etc.) from the platinum(IV) therapeutically active precursor may form a platinum(II) therapeutically active agent or a second generation precursor to a platinum(II) therapeutically active agent. In some cases, one, two, three, or four of $R^3$, $R^4$, $R^5$ and/or $R^6$ may be released from the platinum(IV) therapeutically active precursor, thereby forming a platinum(II) therapeutically active agent. In some cases, as described herein, one or more ligands or groups (e.g., $R^7$ and/or $R^8$, as described herein) may associate with the platinum(II) therapeutically active agent upon dissociation of the one or more ligands. The therapeutically active platinum(II) agent may be useful for the treatment of cancer. In some cases, the release of at least one ligand (e.g., $R^5$ and $R^6$) from the platinum center may be facilitated by a redox change of the platinum(IV) center. In some cases, the redox change may be caused by the release of $R^5$ and $R^6$ from the platinum(IV) center. In other cases, a redox change of the platinum(IV) center may promote the release of $R^5$ and $R^6$. For example, a redox change of the platinum(IV) center may cause a change in coordination geometry for the metal ion that reduces the number of ligands, thereby causing $R^5$ and $R^6$ to dissociate from the metal center. As another example, the redox change of a platinum(IV) center may promote the lability of one or more ligands (e.g., $R^3$, $R^4$, $R^5$, and/or $R^6$) and make it more likely that the one or more ligands (e.g., $R^3$, $R^4$, $R^5$, and/or $R^6$) may be replace by other ligands.

In some cases, the precursor to a therapeutically active agent may form, upon release, a therapeutically active agent or a second generation precursor to a therapeutically active agent. The second generation precursor to a therapeutically active agent may be chemically alter, transformed, and/or activated upon release from the composition (e.g., upon reduction of a Pt(IV) center to a Pt(II) center) to form the therapeutically active agent. For example, the second generation precursor to a therapeutically active agent may comprise a functional group which may undergo a chemical reaction (e.g., in situ, upon exposure to a cellular environment) to form a therapeutically active agent. As a specific non-limiting example, the second generation precursor may comprise a carboxylic group, which may undergo transformation in situ to form an alcohol or ester, which may be a therapeutically active composition. As another example, the replacement of a ligand on a second generation precursor of a therapeutically active platinum agent may form a therapeutically active platinum agent.

In some embodiments, the release rate of the second therapeutically active agent (or precursor) from the platinum(IV) compound may be altered based on the nature of the second therapeutically active agent and/or by altering the tether used in association of the second therapeutically active agent with the platinum center. This may be due to a change in the redox properties of the platinum center. For example, a first $R^5$ group may allow for the reduction of the Pt(IV) center more readily than a second $R^5$ group, which may lead to the release of the first $R^5$ group (e.g., a second therapeutically active agent) at a different rate than the release of the second $R^5$ group. In one embodiment of the present invention, the release rate of a selected second therapeutically active agent may be adjusted by modifying the nature of the tether (e.g., the type of functional group, carbon chain length, etc.).

In some embodiments, the ligands of the composition may be selected such that upon reduction of the metal center, one or more ligands may be released and selected platinum(II) therapeutically active agent or second generation precursor to a platinum(II) therapeutically active agent is formed. For example, $R^1$, $R^2$, $R^3$, and $R^4$ may be selected such that, upon reduction of the platinum metal center and release of $R^5$ and $R^6$ (as described herein), a selected platinum(II) therapeutically active agent is formed. As another example, $R^1$, $R^2$, may be selected such that, upon reduction of the platinum metal center, release of $R^3$, $R^4$, $R^5$ and $R^6$, and association of $R^7$ and $R^8$ (as described herein), a selected platinum(II) therapeutically active agent is formed. The therapeutically active platinum(II) agent may be any known platinum(II) therapeutically active agent. Non-limiting examples of platinum(II) therapeutically active agents include cisplatin ([cis-Pt(NH$_3$)$_2$Cl$_2$]), carboplatin ([cis-Pt(NH$_3$)$_2$(1,1-(OCO)C$_4$H$_6$)]), oxaliplatin, [cis-Pt(NH$_3$)$_2$(trans-1,2-(OCO)$_2$C$_6$H$_{10}$], [cis-Pt(DACH)Cl$_2$] (where DACH is diaminocyclohexane), nedaplatin ([cis-Pt(NH$_3$)$_2$OCH$_2$CHO$_2$], stratoplatin, paraplatin, platinol, cycloplatam, dexormaplatin, enloplatin, iproplatin, lobaplatin, ormaplatin, spiroplatin, zeniplatin, etc., as will be known to those of ordinary skill in the art. FIG. 1 shows some non-limiting examples of examples of platinum(II) therapeutically active agents.

In some embodiments, the ligands associated with the platinum center in the therapeutically active platinum compound (e.g., $R^1$-$R^4$) may include functional groups capable of interaction with a metal center, e.g., heteroatoms such as nitrogen, oxygen, sulfur, and phosphorus. Non-limiting examples of compounds which the ligands may comprise include amines (primary, secondary, and tertiary), aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands (e.g., $R^1$-$R^4$) may be aryl group, alkenyl group, alkynyl group or other moiety which may bind the metal atom in either a sigma- or pi-coordinated fashion. In some cases, $R^1$ and $R^2$ may be labile ligands and $R^3$ and $R^4$ may be non-labile ligands covalently bonded to the platinum metal center.

In some embodiments, any two or three of $R^1$, $R^2$, $R^3$, and $R^4$ can be joined together to form a bidentate ligand or tridentate ligand. A bidentate ligand when bound to a metal center, forms a metallocycle structure with the metal center. Bidentate ligands suitable for use in the present invention include species which have at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, alkyl and aryl derivatives of moieties such as amines, phosphines, phosphites, phosphates, imines, oximes, ethers, hybrids thereof, substituted derivatives there of, aryl groups (e.g., bis-aryl, heteroaryl-substituted aryl), heteroaryl groups, and the like. Specific examples of bidentate ligands include ethylene diamine, 2,2'-bipyridine, acetylacetonate, oxalate, and the like. Non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

In some embodiments, compounds of the invention may comprise a tridentate ligand, which includes species which have at least three sites capable of binding to a metal center. For example, the tridentate ligand may comprise at least three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties, triimidazoyl moieties, tris pyrazoyl moieties, and combinations of the above ligands.

Pt(II) and Pt(IV) complexes of the invention may be synthesized according to methods known in the art, including various methods described herein. For example, the method may comprise reaction of cisplatin with one or more ligand sources. In some cases, a Pt(IV) complex, wherein $R^5$ and $R^6$ are —OH, can be obtained by reaction of the parent Pt(II) species with, for example, hydrogen peroxide at temperatures ranging between about 25 and about 60° C. in an appropriate solvent, such as water or N,N-dimethylformamide. The desired Pt(IV) complex may synthesized comprising selected $R^5$ and $R^6$ groups according to method known in the art, for example, by functionalization of the —OH groups (e.g., by reaction with an anhydride, an isocyanate, a pyrocarbonate, an acid chloride, etc.).

In some embodiments, a platinum complex may comprise one or more leaving groups. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), pyridine, alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride.

Some embodiments of the invention comprise compounds having two leaving groups positioned in a cis configuration, i.e., the compound may be a cis isomer. However, it should be understood that compounds of the invention may also have two leaving groups positioned in a trans configuration, i.e., the compound may be a trans isomer. Those of ordinary skill in the art would understand the meaning of these terms.

Some embodiments of the invention provide the compound as a salt comprising a positively-charged platinum complex and a counterion (e.g., "X"). The counterion X may be a weak or non-nucleophilic stabilizing ion. In some cases, the counterion is a negatively-charged and/or non-coordinating ion. Examples of counterions include halides, such as chloride.

The invention also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having cancer, or of patients susceptible to cancers. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the invention. Such compositions may also be screened by the assays described herein for increased potency and specificity towards a cancer, preferably with limited side effects. Synthesis of such compositions may be accomplished through typical chemical modification methods such as those routinely practiced in the art. Another aspect of the present invention provides any of the above-mentioned compounds as being useful for the treatment of cancer.

The invention further comprises compositions, preparations, formulations, kits, and the like, comprising any of the compounds as described herein. In some cases, treatment of a cancer may involve the use of compositions, as described herein. That is, one aspect of the invention involves a series of compositions (e.g., pharmaceutical compositions) or agents useful for treatment of cancer or tumor. These compositions may also be packaged in kits, optionally including instructions for use of the composition for the treatment of such conditions. These and other embodiments of the invention may also involve promotion of the treatment of cancer or tumor according to any of the techniques and compositions and combinations of compositions described herein.

Aspects of the invention may be used to prevent the growth of a tumor or cancer, and/or to prevent the metastasis of a tumor or cancer. In some embodiments, compositions of the invention may be used to shrink or destroy a cancer. It should be appreciated that compositions of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition of the invention may be administered to a patient who has undergone a treatment involving surgery, radiation, and/or chemotherapy. In certain embodiments, a composition of the invention may be administered chronically to prevent, or reduce the risk of, a cancer recurrence.

In another aspect, the present invention provides "pharmaceutical compositions" or "pharmaceutically acceptable" compositions, which comprise a therapeutically effective amount of one or more of the compounds described herein, formulated together with one or more pharmaceutically acceptable carriers (additives) and/or diluents. As described herein, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain one or more basic functional groups and, thus, are capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," *J. Pharm. Sci.* 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compound may be orally administered, parenterally administered, subcutaneously administered, and/or intravenously administered. In certain embodiments, a compound or pharmaceutical preparation is administered orally. In other embodiments, the compound or pharmaceutical preparation is administered intravenously. Alternative routes of administration include sublingual, intramuscular, and transdermal administrations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with the present invention include time-release, delayed release, sustained release, or controlled release delivery systems, as described herein. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, about 0.1% to about 99.5%, about 0.5% to about 90%, or the like, of active ingredient in combination with a pharmaceutically acceptable carrier.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some cases, the dose may range from between about 5 and about 50 mg of compound per kg of body weight, between about 10 and about 40 mg of compound per kg of body weight, between about 10 and about 35 mg of compound per kg of body weight, or between about 15 and about 40 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The present invention also provides any of the above-mentioned compositions useful for treatment of cancer packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer in treating the pathology, as opposed to the symptoms of the cancer. That is, the kit can include a description of use of the compositions as discussed herein. The kit also can include instructions for use of a combination of two or more compositions of the invention. Instructions also may be provided for administering the drug by any suitable technique, such as orally, intravenously, or via another known route of drug delivery. The invention also involves promotion of the treatment of cancer according to any of the techniques and compositions and composition combinations described herein.

The compositions of the invention, in some embodiments, may be promoted for treatment of abnormal cell proliferation, cancers, or tumors, or includes instructions for treatment of accompany cell proliferation, cancers, or tumors, as mentioned above. In another aspect, the invention provides a method involving promoting the prevention or treatment of cancer via administration of any one of the compositions of the present invention, and homologs, analogs, derivatives, enantiomers and functionally equivalent compositions thereof in which the composition is able to treat cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, cancers or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As used herein, a "subject" or a "patient" refers to any mammal (e.g., a human), such as a mammal that may be susceptible to tumorigenesis or cancer. Examples include a human, a non-human primate, a cow, a horse, a pig, a sheep, a goat, a dog, a cat, or a rodent such as a mouse, a rat, a hamster, or a guinea pig. Generally, or course, the invention is directed toward use with humans. A subject may be a subject diagnosed with cancer or otherwise known to have cancer. In certain embodiments, a subject may be selected for treatment on the basis of a known cancer in the subject. In some embodiments, a subject may be selected for treatment on the basis of a suspected cancer in the subject. In some embodiments, a cancer may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compositions of the invention to the subject. In some embodiments, the composition may be administered to prevent the development of a cancer. However, in some embodiments, the presence of an existing cancer may be suspected, but not yet identified, and a composition of the invention may be administered to prevent further growth or development of the cancer.

It should be appreciated that any suitable technique may be used to identify or detect mutation and/or over-expression associated with a cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.).

The presence of a cancer can be detected or inferred by detecting a mutation, over-expression, amplification, or any combination thereof at one or more other loci associated with a signaling pathway of a cancer.

A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a cancer. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more compounds may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more compounds described herein in an amount effective to treat one or more cancers described herein.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.
The term "aryloxy" refers to the group, —O-aryl.
The term "acyloxy" refers to the group, —O-acyl.
The term "aralkyl" or "arylalkyl," as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence. An example of a substituted amine is benzylamine. Another non-limiting example of an amine is cyclohexylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl,-carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following references are herein incorporated by reference: U.S. Provisional Patent Application Ser. No. 61/091,977, filed Aug. 26, 2008, entitled "Mitochondria Targeting Platinum(IV) Complexes with Dual Cell Killing Modes," by Lippard, et al., and U.S. Provisional Patent Application Ser. No. 61/196,419, filed Oct. 17, 2008, entitled "Dual Mode Pharmaceutical Therapy," by Dhar, et al.

The following examples are intended to illustrate certain embodiments of the present invention, but do not exemplify the full scope of the invention.

EXAMPLE 1

Figure 2:
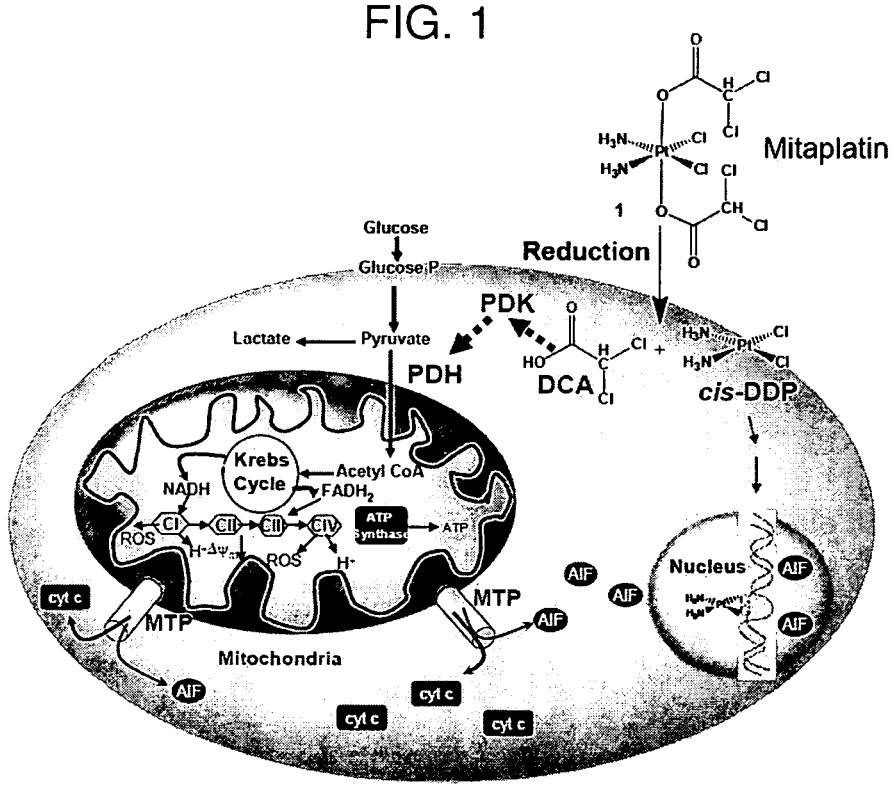
FIG. 2 illustrates the structure of a non-limiting composition of the present invention, according to one embodiment, and the proposed cellular pathway of action.

Recently, the mitochondrion has been recognized as a novel target for anticancer therapy due to its crucial role involved in arbitrating cell apoptosis. Dichloroacetic acid (DCA) is an anticancer agent with potent activity and little apparent toxicity. DCA attacks the mitochondria of cancer cells, driving them to commit cellular suicide, or apoptosis. Unlike other anticancer drugs, in most embodiments, DCA does not appear to have any deleterious effect on normal cells. DCA reverses the mitochondrial changes in a wide range of cancers, making malignant cells more vulnerable to normal cell death programs. Cancer cells generally use glycolysis rather than glucose oxidation for energy. The body often kills damaged cells by apoptosis, a mechanism of cellular self-destruction that involves mitochondria, but this mechanism fails in cancer cells. The apoptotic resistance is due to hyperpolarization of the mitochondrial membrane, which prevents release of pro-apoptotic mediators from mitochondria to the cytoplasm. DCA has the ability to change the metabolism in mitochondria. The dichloroacetate ion stimulates the activity of the mitochondrial enzyme pyruvate dehydrogenase (PDH) by inhibiting the enzyme pyruvate dehydrogenase kinase (PDK). FIG. 2 illustrates the structure of Mitaplatin (compound 1) and the proposed cellular pathway of mitaplatin action. In some cases, DCA shifts the metabolism from glycolysis to glucose oxidation, which decreases the mitochondrial membrane potential, or $\Delta\psi_m$. This activity helps to open mitochondrial transition pores (MTP), thus allowing the translocation of proapoptotic mediators like cytochrome c (cyt c) and apoptosis inducing factor (AIF), leading to apoptosis. DCA, an orphan drug, is not approved for use by the medical community in cancer therapy, and cancer patients are warned not to treat themselves with substances that can be purchased from chemical companies. DCA, being an orphan drug, is both non-patentable and readily available.

A Pt(IV) compound (compound 1 or Mitaplatin) having two DCA moieties at the axial sites was synthesized in order to investigate whether DCA released inside the cells by the reduction of the Pt(IV) complex, would alter their mitochondrial metabolism pathway. Mitaplatin may exhibit dual killing modes towards cancer cells, one in which cisplatin interacts with its key target, nuclear DNA, and the other, DCA released upon reduction, follows a pathway which induces mitochondria-dependent apoptosis by mitochondrial depolarization and efflux of proapoptotic mediators.

Mitaplatin was prepared from a reaction of c,c,t-[Pt(NH$_3$)$_2$Cl$_2$(OH)$_2$] with dichloroacetic anhydride in >50% yield. Formation of compound 1 was evidenced by the disappearance of the O—H stretching band of the starting compound and the presence of C=O stretching at 1651 cm$^{-1}$ in the infrared spectra. The presence of compound 1 was also confirmed by $^1$H, $^{13}$C and $^{195}$Pt NMR and HRMS. Mitaplatin was also characterized by single crystal X-ray crystallography. Compound 1 crystallized as light yellow blocks in the triclinic space group P1 with two molecules of DMF per molecule. The unit cell contained one unique molecular conformation of the metal complex. Crystallographic data and selected bond distances and angles are provided. The structure of the complex comprises a discrete monomeric species with the platinum in octahedral coordination geometry. The donor atoms in the basal plane are two nitrogen atoms from two amines and two chloride atoms. Two carboxylate groups from two DCA molecules are bonded at the apical site. The Pt—N and Pt—Cl distances are ~2.4 and 2.25 Å, respectively.

Compound 1 is redox-active and displayed irreversible cyclic voltammetric responses for the Pt(IV)/Pt(II) couple near −0.173 V vs Ag/AgCl at pH 7.4 and the value at pH 6.0 is −0.152 vs. Ag/AgCl. The reduction potentials at various pH suggested that this compound would be easily reduced inside cells. Without wishing to be bound by theory, this low reduction potential may be due to the presence of chlorine atoms from DCA near the metal centre. The cathodic reduction potential depends on the electron-withdrawing power of the axial ligands and the bulkiness of the axial or carrier ligands.

Figure 3:
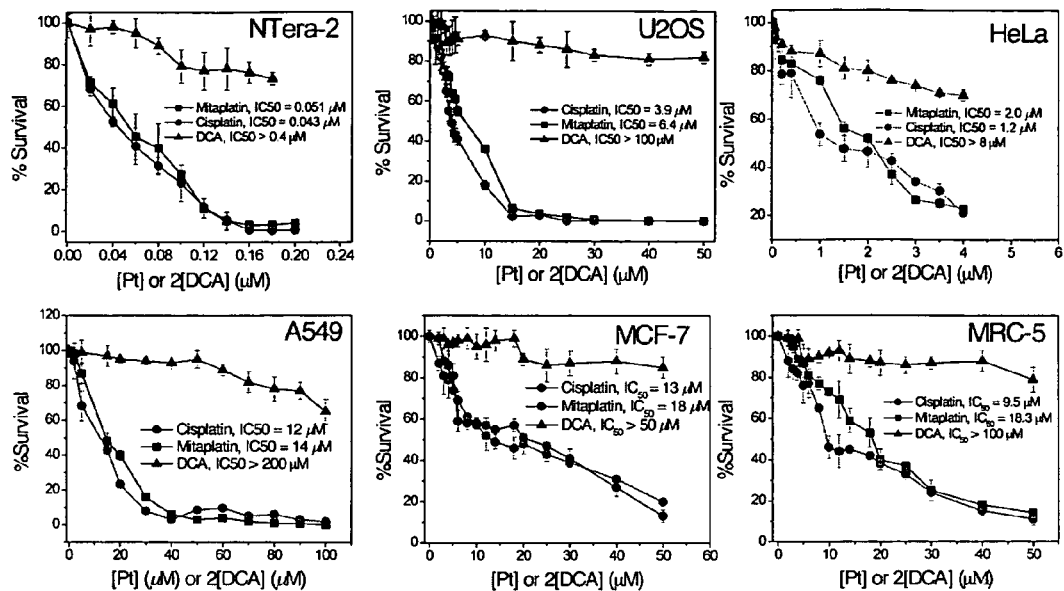
FIG. 3 shows a plot of the cytotoxicity of a non-limiting composition, cisplatin, and DCA against NTera-2, U2OS, HeLa, A549, and MCF-7 cancer cells, and MRC-5 normal cells, according to some embodiments.

The ability of the compound 1 to promote cell death was determined using the MTT assay and the results were compared against those for cisplatin or -2 DCA using NTera, HeLa, U2OS, A549, and MCF-7 cancer cells as well as MRC-5 normal fibroblasts (FIG. 3). Results are presented in Table 1. Mitaplatin has an IC$_{50}$ value of 0.051 µM, comparable to that of cisplatin (IC$_{50}$, 0.043 µM), in cisplatin-sensitive testicular NTera-2 cells and more toxic than DCA alone. In U2OS osteosarcoma cells, cisplatin has an IC50 of 3.9 µM, whereas that of mitaplatin is 6.4 µM. Similarly, in HeLa cervical cancer cells, comparable IC50 values for mitaplatin and cisplatin were observed, 2.0 µM and 1.20 µM, respectively. Control experiments with the well-known platinum (IV) compound c,c,t-[Pt(NH$_3$)$_2$Cl$_2$(O$_2$CCH$_3$)$_2$], a close analogue of satraplatin, revealed it to be less active by several fold than mitaplatin in all cells. This enhanced potency of mitaplatin is consistent with the expected dual killing mechanism.

TABLE 1

Cell killing ability of mitaplatin. Comparison of IC$_{50}$ values for mitaplatin, cisplatin, and DCA against cancer and normal cells as determined by a MTT assay.

| Cell lines* | IC$_{50}$ (µM) | | |
| --- | --- | --- | --- |
| | Cisplatin | Mitaplatin | DCA |
| NTera-2 | 0.043 | 0.051 | >0.4 |
| HeLa | 1.2 | 2.0 | >8.0 |
| U2OS | 3.9 | 6.4 | >100 |
| A549 | 12.0 | 14.0 | >200 |
| MCF-7 | 13.0 | 18.0 | >100 |
| MRC-5 | 9.5 | 18.3 | >100 |
| A2780 | 0.56 | 1.1 | >120 |
| A2780/CP70 | 6.0 | 3.34 | >120 |

*NTera-2, human testicular cancer; HeLa, human cervical cancer; U2OS, human osteosarcoma; A549, human lung carcinoma; MCF-7, human breast adenocarcinoma; MRC-5, normal lung fibroblast; A2780, human ovarian carcinoma; A2780/CP70, cisplatin-resistant human ovarian carcinoma.

The following describes a mitochondrial membrane potential assay using compound 1. JC-1 Assay: Mitochondrial attack is associated with a drop in mitochondrial transmembrane potential ($\Delta\psi_m$). For this reason $\Delta\psi_m$ is an important parameter of mitochondrial function and has been used as an indicator for mitochondrial death. Variation in $\Delta\psi_m$ can be studied by evaluating the changes in fluorescence intensity of cells stained with lipophilic cationic dye, 5,5',6,6'-tetrachloro-1,1',3,3'-tetraethylbenzimidazolylcarbocyanine iodide (JC-1). It can selectively enter mitochondria and reversibly change color from green to red as the membrane potential increases.

Figure 4:
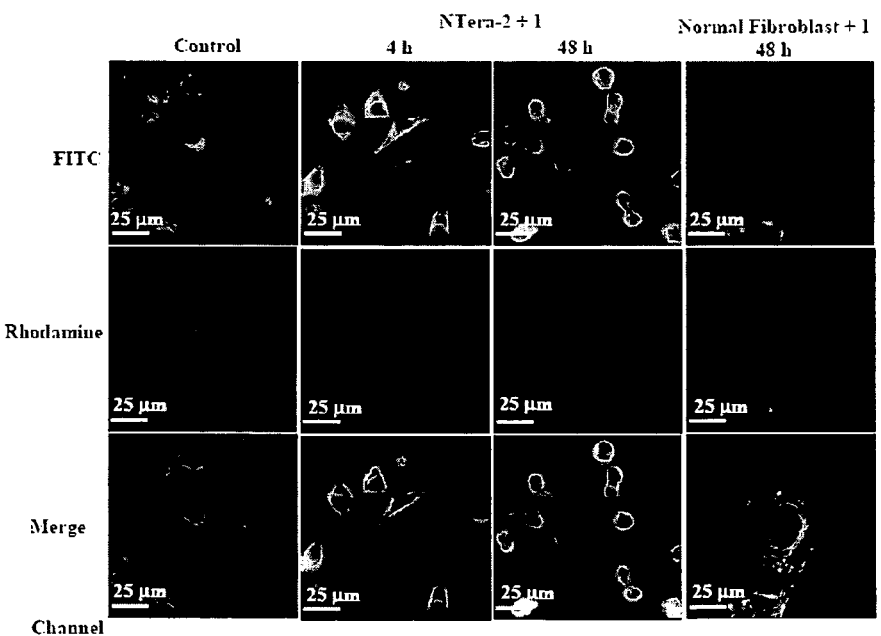
FIGS. 4 and 5 show fluorescent images of cancer cells and non-cancerous cells following exposure to a non-limiting composition of the present invention, according to one embodiment.

The negative charge established by the mitochondrial membrane potential allows the lipophilic dye, bearing a delocalized positive charge, to enter the mitochondria where it accumulates. When the critical concentration is exceeded, J-aggregates form, which becomes red. In apoptotic cells, the mitochondrial membrane potential collapses, and the JC-1 can not accumulate within the mitochondria. In these cells, JC-1 remains in the cytoplasm in a green fluorescent monomeric form. Apoptotic cells, showing primarily green fluorescence, are easily differentiated from the healthy cells which show mainly red fluorescence. FIG. 4 shows that compound 1 attacks the mitochondria of the human cancer NTera-2 cells but had no effect on the healthy normal fibroblast cells.

Figure 5:
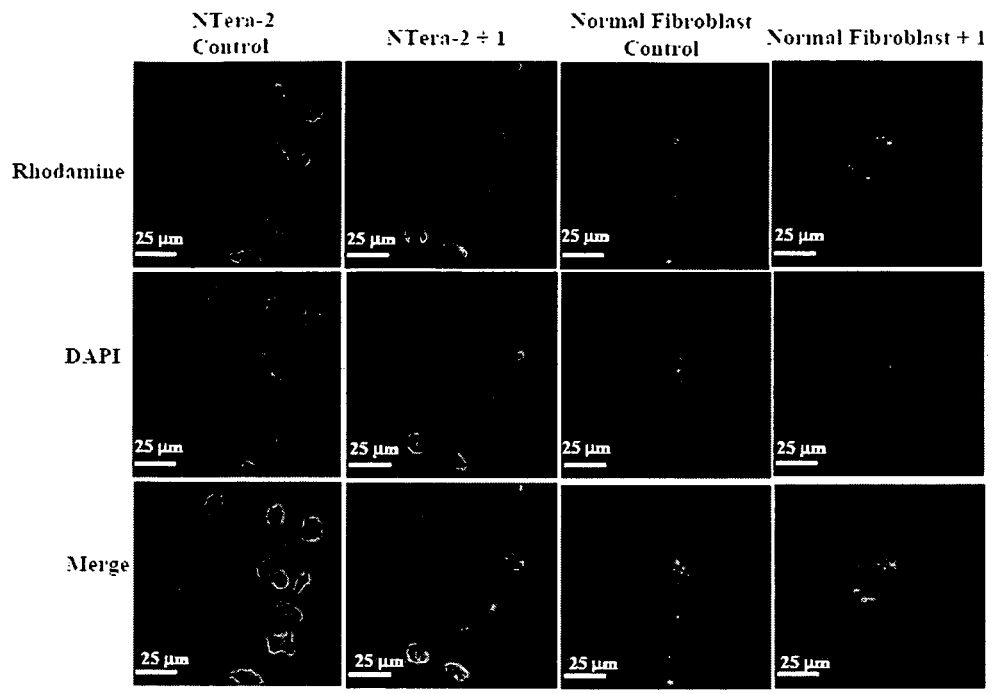

TMRM Assay: Mitochondrial attack by compound 1 was also studied using the TMRM assay as shown in FIG. 5. FIG. 5 shows that compound 1 significantly depolarizes the NTera-2 cells but had no effect on the healthy normal fibroblast cells.

Figure 6:
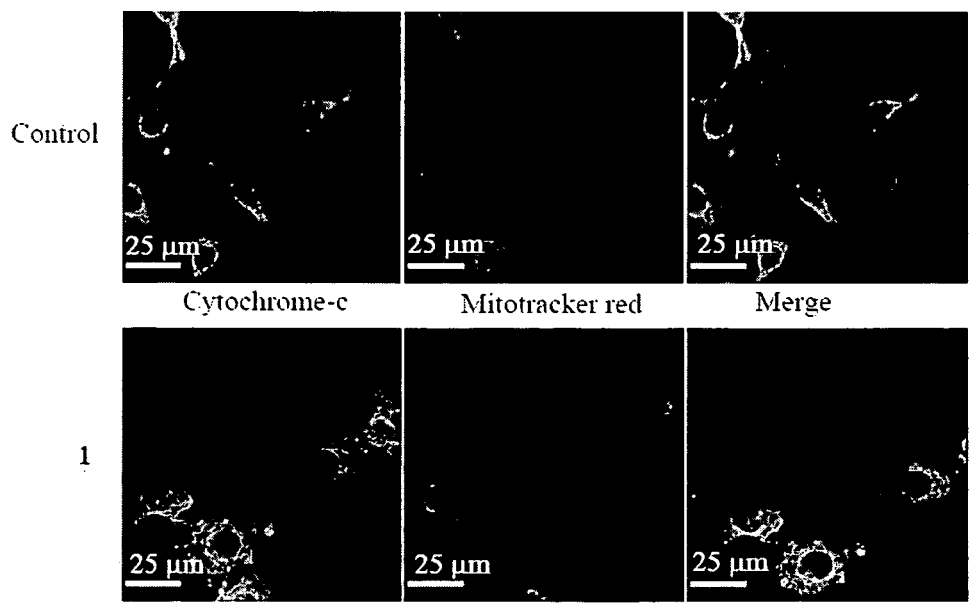
FIG. 6 shows fluorescent images indicating the release of cytochrome c from cells following treatment with a non-limiting composition of the present invention.
Figure 7:
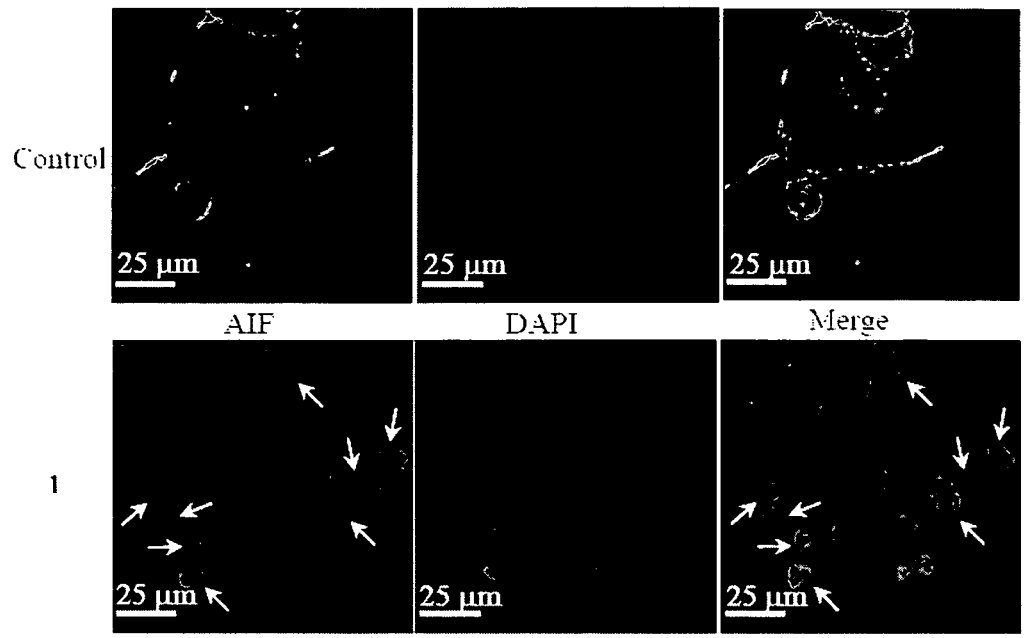
FIG. 7 shows apoptosis and release of apoptosis inducing factor from cells following treatment with a non-limiting composition of the present invention.

It was determined that in the Mitaplatin treated NTera-2 cells, cytochrome c was diffusely distributed in the cytoplasm (FIG. 6) and apoptosis inducing factor AIF (FIG. 7) was located in the nucleus, whereas in the untreated cancer cells, cytochrome c and AIF are both restricted in the mitochondria indicating that DCA, once released upon reduction, leads to a cascade of events leading the cell to commit suicide. FIG. 6 shows cytochrome c release from mitaplatin treated cells. FIG. 7 shows apoptosis and release of apoptosis inducing factor.

Figure 8:
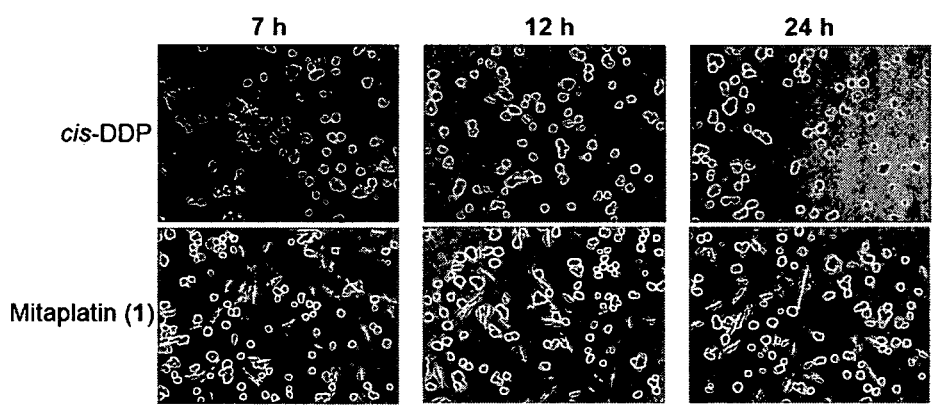
FIG. 8 shows fluorescent images of cancer cells and non-cancerous cells following exposure to a non-limiting composition of the present invention.
Figure 9:
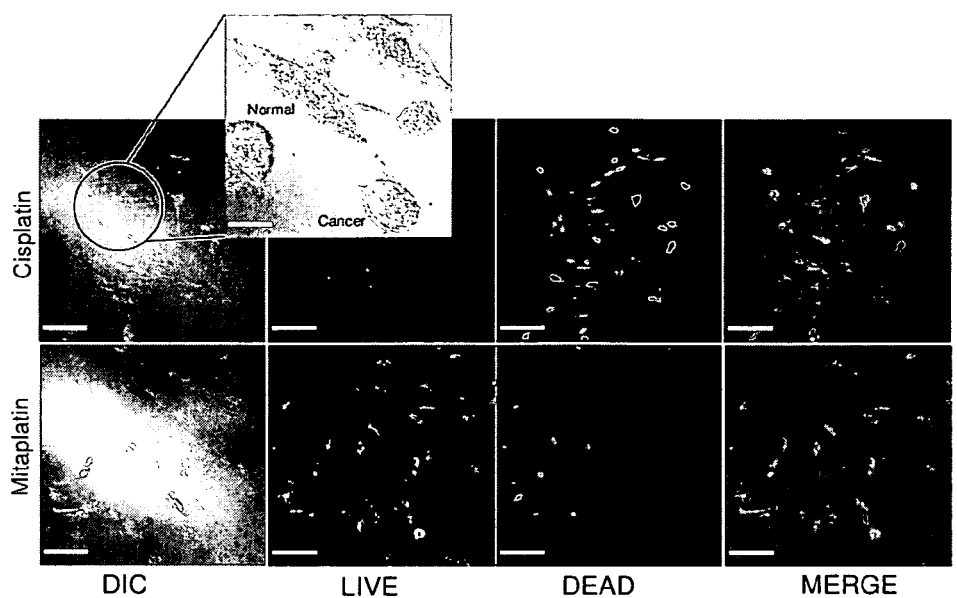
FIG. 9 shows the selective killing of cancerous A549 cells by a non-limiting composition of the present invention in a co-culture with normal MRC-5 cells, according to one embodiment.

It was also determined that, in a co-culture of normal fibroblasts and cancerous NTera-2 cells, cisplatin kills both the normal and cancer cells, whereas Mitaplatin selectively kills the cancer cells (FIG. 8). FIG. 8 shows selective killing ability of mitaplatin (compound 1) towards cancerous NTera-2 cells over the normal fibroblast cells (elongated ones). Cisplatin kills both NTera-2 and normal fibroblast cells Studies were also conducted on a co-culture of human lung cancer A549 cells and normal human lung fibroblasts MRC-5. Selective killing of cancer cells by mitaplatin was demonstrated using a LIVE/DEAD viability assay. The assay allowed for the simultaneous determination of live and dead cells in a co-culture by labeling live cells with calcein AM dye, which fluoresces only when cleaved by intracellular esterase enzymes, and ethidium heterodimer (EthD-1), which only enters dead cells with disrupted cell membranes. FIG. 9 shows the selective killing of cancerous A549 (round) cells by mitaplatin in a co-culture with normal MRC-5 (elongated) cells assayed using LIVE/DEAD staining. Following mitaplatin or cisplatin exposure for 24 h, cells were stained with calcein AM (green fluorescence) and ethidium homodimer-1 (red fluorescence) to differentiate between live and dead cells, respectively. These results indicate that, unlike cisplatin, mitaplatin selectively induced cell death in human cancer A549 cells, but not in normal MRC-5 cells under the similar treatment conditions.

Figure 10A:
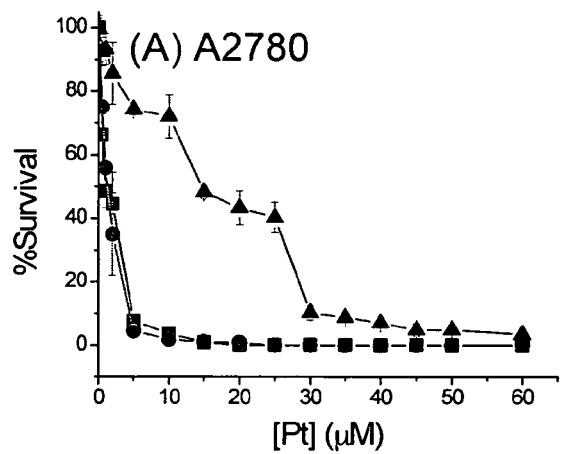
FIG. 10 shows cytotoxicity profiles of a non-limiting composition of the present invention (•), cisplatin (■), and c,c,t-[Pt(NH$_3$)$_2$Cl$_2$(O$_2$CCH$_3$)$_2$] (▲) with (A) cisplatin sensitive A2780 cells and (B) cisplatin resistant A2780/CP70 cells.
Figure 10B:
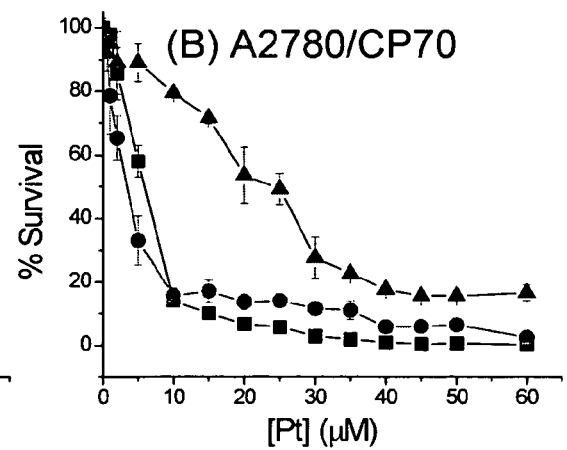

In some cases, mitochondrial defects may be associated with cisplatin resistance phenotypes, and several hypotheses have been suggested to explain this observation. A more negative membrane potential might promote translocation of the active, cationic form of cisplatin from the cytoplasm to mitochondria, thus diminishing platination of nuclear DNA. This effect would suggest, in some embodiments, that a combination of cisplatin with a mitochondrial targeting moiety may be an attractive therapeutic strategy for attacking cisplatin-resistant tumors. Thus, a pair of cisplatin sensitive A2780 and resistant A2780/CP70 ovarian cancer cells were studied (Table 1 and FIG. 10). Specifically, FIG. 10 shows the cytotoxicity profiles of mitaplatin (•), cisplatin (■), and c,c,t-[Pt(NH$_3$)$_2$Cl$_2$(O$_2$CCH$_3$)$_2$] (▲) with (A) cisplatin sensitive A2780 cells and (B) cisplatin resistant A2780/CP70 cells, after 72 h as determined by the MTT assay. The controls were cisplatin and c,c,t-[Pt(NH$_3$)$_2$Cl$_2$(O$_2$CCH$_3$)$_2$]. The cells displayed a low level of resistance to mitaplatin (IC$_{50}$ for A2780, 1.1 µM; IC$_{50}$ for A2780/CP70, 3.34 µM) as compared to cisplatin (corresponding IC$_{50}$ values of 0.56 µM and 6.0 µM). Results for the A2780/CP70 cells indicate that DCA plays a role, in this embodiment, in making cisplatin-resistant cells susceptible towards mitaplatin treatment. A2780/CP70 cells were much more resistant to the control platinum(IV) compound c,c,t-[Pt(NH$_3$)$_2$Cl$_2$(O$_2$CCH$_3$)$_2$].

In order to quantify mitaplatin-induced apoptosis in cancer cells, an Annexin-V was performed and analyzed using flow cytometry. With this analysis, the percentage of apoptotic cells found was determined at 72 h after exposure of mitaplatin and cisplatin. Apoptosis was detected in cancerous U2OS, HeLa, and A549 cells with 10 and 20 µM mitaplatin and cisplatin. Cisplatin at 10 µM concentration showed apoptosis in normal MRC-5 cells whereas mitaplatin did not show any detectable apoptosis with these normal cells.

A Pt(IV) prodrug containing two DCA molecules at the axial sites which releases two molecules of mitochondria targeting DCA moieties by intracellular reduction was prepared and characterized. This compound shows very high toxicity with human testicular cancer NTera-2 cell lines. Compound 1 showed (IC$_{50}$, 0.051 µM) comparable IC$_{50}$ value to cis-DDP (IC$_{50}$, 0.05 µM). It was observed that compound 1 reverses the hyperpolarization of NTera-2 cells and returned the mitochondrial membrane potential ($\Delta\psi_m$) to the level of the normal cells, in contrast, this compound does not change the $\Delta\psi_m$ of the normal fibroblasts. It was also determined that compound 1 treated NTera-2 cells, cytochrome c was diffusely distributed in the cytoplasm and apoptosis inducing factor AIF was located in the nucleus, whereas in the untreated cancer cells, cytochrome c and AIF both are restricted to the mitochondria indicating that DCA, once released upon reduction, leads to a cascade of events leading to commit cellular suicide. Mitaplatin attacks mitochondria as well as the nucleus selectively in cancer cells. This new methodology of using compounds with dual killing modes towards cancer cells where platinum centre interacts with its own target, nuclear DNA, whereas DCA once released upon reduction attacks mitochondria would be attractive to design new platinum drug candidates.

EXAMPLE 2

The following example outlines the materials and methods used in example 1.

Materials and Measurements. The complexes cis-[Pt(NH$_3$)$_2$Cl$_2$], and c, c, t-[Pt(NH$_3$)$_2$Cl$_2$(OH)$_2$] were synthesized as previously described. Distilled water was purified by passage through a Millipore Milli-Q Biocel water purification system (18.2 MΩ) with a 0.22 µm filter. For the detection of cisplatin 1,2-d(GpG) intrastrand adduct, a monoclonal adduct specific antibody R-C18 was used which was a gift from Anti-cytochrome c (Ab-1) sheep polyclonal antibody was procured from Calbiochem. For AIF detection, rabbit polyclonal IgG antibody was used from Santa Cruz Biotechnology, Inc.

Alexa Fluor® 488 labeled secondary antibody donkey anti-(sheep IgG) was obtained from Invitrogen for cytochrome c detection. For AIF detection, Alexa Fluor® 546 labeled secondary antibody goat anti-(rabbit IgG) was purchased from Invitrogen. Dr. Jürgen Thomale, University of Duisburg-Essen Hufelandstr, Germany. Specific adhesion slides for immunofluoresecence were purchased from Squarix Biotechnology, Marl, Germany. JC-1 (5,5', 6,6'-tetrachloro-1,1', 3,3' tetraethylbenzimidazolylcarbocyanine iodide) was obtained from Cayman Chemicals. $^1$H NMR and $^{195}$Pt NMR spectra were recorded on a Bruker AVANCE-400 NMR spectrometer with a Spectro Spin superconducting magnet in the Massachusetts Institute of Technology Department of Chemistry Instrumentation Facility (MIT DCIF). Atomic absorption spectroscopic measurements were taken on a Perkin Elmer AAnalyst 300 spectrometer. HRMS analysis was carried out on a Bruker Daltonics APEXIV 4.7 Tesla Fourier Transform Ion Cyclotron Resonance mass spectrometer in the MIT DCIF. Electrochemical measurements were performed at 25° C. on a 263 EG&G Princeton Applied Research electrochemical analyzer with electrochemical analysis software 270 using a three electrode set-up comprising a glassy carbon working electrode, platinum wire auxiliary electrode and an Ag/AgCl reference electrode. The electrochemical data were uncorrected for junction potentials. KCl was used as supporting electrolyte. Fluorescence imaging studies were performed with an Axiovert 200M inverted epifluorescence microscope (Zeiss, Thornwood, N.Y.) equipped with an EM-CCD digital camera C9100 (Hamamatsu, Japan). An X-Cite 120 metal-halide lamp (EXFO, Quebec, Canada) was used as the light source. The microscope was operated with Volocity software (Improvision, Lexington, Mass.).

Synthesis of c,c,t-[Pt(NH$_3$)$_2$Cl$_2$(O$_2$CCHCl$_2$)$_2$] (1). To a solution of c, c, t-[Pt(NH$_3$)$_2$Cl$_2$(OH)$_2$] (0.2 g, 0.6 mmol) in DMF (5 mL) was added dichloroacetic anhydride (0.28 g, 1.5 mmol) and the reaction mixture was stirred at room temperature for 4 h. Diethyl ether was added to the mixture to precipitate a light yellow solid, which was washed several times with diethyl ether and dried. Compound 1 was isolated in 55% (0.29 g) yield. IR (KBr): $v_{max}$ 3178, 3076, 3012, 1651, 1568, 1435, 1333, 1214, 1103, 1021, 819, 789, 723, 666, 582 cm$^{-1}$; ESI-HRMS (M-H) Calcd.=554.8145, Found=554.8138.

X-ray Crystallographic Procedures. The structure of c,c,t-[Pt(NH$_3$)$_2$Cl$_2$(O$_2$CCHCl$_2$)$_2$] (compound 1) was obtained by single crystal X-ray diffraction technique. All geometric and intensity data were collected at 110 K using a Bruker SMART Apex CCD diffractometer with a graphite-monochromated Mo—K$_\alpha$ radiation ($\lambda$=0.71073 Å). The SMART software was used for data acquisition and SAINT for data integration. Full-matrix least-squares refinement was carried out on F$^2$ values using the SHELXTL software, and empirical absorption corrections were applied with SADABS. All non-hydrogen atoms were located and their positions were refined with anisotropic thermal parameters by successive least-squares cycles and Fourier syntheses. Perspective view of the molecule was obtained by ORTEP.

Electrochemistry. Electrochemical measurements were made at 25° C. on a EG&G PAR Model 263 Potentiostat/Galvanostat with electrochemical analysis software 270 and a three electrode set-up comprising a glassy carbon working electrode, platinum wire auxiliary electrode and an Ag/AgCl reference electrode. The electrochemical data were uncorrected for junction potentials. KCl was used as a supporting electrolyte.

Cytotoxicity Study:

Cell Line and Cell Culture. Healthy normal fibroblast GM61869, human cancer NTera-2, human cervical cancer HeLa, human osteosarcoma cell line U2OS were obtained from the ATCC. Cells were incubated at 37° C. in 5% CO$_2$ and grown in DMEM medium supplemented with 10% fetal bovine serum and 1% penicillin/streptomycin. Cells were passed every 3 to 4 days and restarted from the frozen stock upon reaching pass number 20.

MTT Assay. Cytotoxic behavior of compound 1, DCA and cis-DDP were evaluated using the MTT assay. Solutions of the platinum complexes were freshly prepared in sterile PBS before use and quantitated by atomic absorption spectroscopy. Cells were seeded on a 96 well plate (1000 cells per well for NTera-2, U2OS, HeLa; 1400 per well for normal fibriblast; 500 per well for 7B, 10B, 175F and 150×2) in 100 µL DMEM media and incubated for 24 hours. The cells were then treated with compound 1, DCA or cis-DDP, separately at varying concentrations and incubated for 72 hours at 37° C. The cells were then treated with 20 µL of 3-(4,5-dimethylthiazol-2-yl)-2,5-diphenyltetrazolium bromide (MTT) (5 mg/mL in PBS) and incubated for 5 h. The medium was removed, the cells were lysed by adding 100 µl, of DMSO, and the absorbance of the purple formazan was recorded at 550 nm using a BioTek Synergy HT multi-detection microplate plate reader. Each well was performed in triplicate in three independent experiments for each cell line.

Fluorescence Imaging:

Cell Fixing Solution. Paraformaldehyde (4.0 g) and NaOH (0.4 g) were dissolved in 100 mL of distilled water. To this solution NaH$_2$PO$_4$ (1.68 g) was added and the pH was adjusted to be in-between 7.5 to 8.0 by adding NaOH.

Fluorescence Sample Mounting Media. For sample mounting, a solution containing 20 mM tris (pH 8.0), 0.5% N-propyl gallate and 50-90% glycerol was used.

Immunofluorescence:

Detection of cytochrome c and AIF. Normal fibroblast or Ntera-2 cells were seeded on microscope coverslips (1 cm) at a confluence of 1600 cells per slip and incubated overnight at 37° C. in DMEM. The medium was changed and compound 1 was added to a final 500 µM. The cells were incubated for 24 or 48 h at 37° C. Medium was then removed and the cells were incubated with fixing solution for 1 h at room temperature followed by three washes with phosphate buffered saline (PBS, pH 7.4). Cells were then fixed with 4% paraformaldehyde in 0.1 M phosphate buffer (pH 7.4) at room temperature for 1 h, washed twice with PBS. Cells were then permeabilize with 0.1% Triton-X100 in PBS for 30 min, followed by six washes with PBS. Cells were then rinsed with blocking buffer (PBS, 0.1% goat serum, 0.075% glycin). Cells were then incubated for 1 h at 37° C. with the anti-cytochrome c (anti-cytochrome c (Ab-1) Sheep pAb, Calbiochem) antibody or AIF (AIF (H-300), Santa Cruz Biotechnology Inc.) antibody both diluted 1:50 in blocking buffer, washed twice with blocking buffer and incubated at 37° C. with Alexa Fluor 488 donkey anti sheep IgG (Invitrogen) antibody for cytochrome c release and Alexa Fluor 546 goat anti-rabbit IgG (Invitrogen) antibody for AIF (dilution 1:50 in blocking buffer) for 1 h. After two washes with blocking buffer and four washes with water, Mitrotacker Red for cytochrome a release and Hoeschst bis-benzamide for AIF release were used to stain mitochondria and nucleus, respectively. They were mounted on microscope slides using mounting solution for imaging.

Detection of cisplatin 1,2-d(GpG) intrastrand adduct. Detection platinum 1,2-d(GpG) adduct was carried out by following a procedure recently reported using an antibody specific to this adduct. Briefly, Ntera-2 cells were seeded in a six well plate using DMEM medium and incubated overnight at 37° C. Compound 1 was added to a final concentration of 20 µM and incubated at 37° C. After 4 h, cells were trypsinized, washed with PBS, the cells were resuspended in HAES-sterile-PBS at a density of $1\times10^6$ per mL and placed onto a pre-coated slide (ImmunoSelect, Squarix) and air dried. Cell fixing was carried out at −20° C. in methanol for 45 min. Nuclear DNA was denatured by alkali (70 mM NaOH, 140 mM NaCl, 40% methanol v/v) treatment for 5 min at 0° C., and cellular proteins were removed by proteolytic procedure involving two steps. The cells were first digested with pepsin at 37° C. for 10 min and then with proteinase K at 37° C. for 5 min. After blocking with milk (1% in PBS; 30 min; 25° C.) slides were incubated with anti-(Pt-DNA) Mabs (R-C18 0.1 mg/mL in milk) for overnight at 4° C. After washing with PBS, immunostaining was performed by incubation with FITC-labeled goat anti-(rat Ig) antibody at 37° C. for 1 h. The nuclei of the cells were stained by using Hoechst (H33258) (250 µg/L) and mounted using the mounting solution for imaging.

Mitochondrial Membrane Potential Assay:

JC-1 Assay. Normal and NTera-2 cells were cultured on cover slips to a density of $1\times10^6$ cells/mL and incubated overnight at 37° C. Cells were then treated with 100 µM of compound 1 or DCA for 4 h and 48 h at 37° C. A solution of JC-1 reagent (Cayman Chemicals; 10 µg/mL in DMEM) was added and incubation was carried out at 37° C. for 30 min. The cells were washed with PBS for five times, fixed in 4% paraformaldehyde and mounted onto glass slides using the procedure as described above.

TMRM Assay. Analysis of mitochondrial membrane potential ($\Delta\psi_m$) was carried out by using tetramethyl rhodamine methyl ester (TMRM). A similar procedure as mentioned above for the JC-1 assay was followed. Before fixing the cells, they were treated with 2 µM of TMRM for 30 min at 37° C.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A composition of matter, comprising:
a compound having the formula,

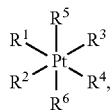

wherein:
$R^1$, $R^2$, $R^3$, and $R^4$ can be the same or different and each is a group comprising at least one of ammonia, an amine, an aryl group, a heterocycle including at least one nitrogen, or a leaving group, any being optionally substituted, or, any two or three of $R^1$, $R^2$, $R^3$ and $R^4$ can be joine together to form a bidentate ligand or tridentate ligand, any being optionally substituted; and
$R^5$ and $R^6$ can be the same or different and at least one is a therapeutically active, or a precursor of a therapeutically active compound, when dissociated from the platinum, wherein the therapeutically active compound selectively affects a cellular pathway of a cancer cell and is substantially inactive toward non-cancerous cells, and wherein at least one of $R^5$ or $R^6$ comprises the group, —OC(O)(CHCl$_2$).

2. The composition of claim 1, wherein each of $R^5$ and $R^6$ comprise the group, —OC(O)(CHCl$_2$).

3. The composition of claim 1, wherein each of $R^1$ and $R^2$ comprise the group, NH$_3$.

4. The composition of claim 1, wherein the therapeutically active compound is dissociated from the platinum center upon reduction of the platinum center.

5. The composition of claim 1, wherein the dissociation of $R^5$ and $R^6$ from the platinum center forms a compound having the formula,

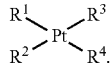

6. The composition of claim 1, wherein the composition, prior to uptake into a cell, is substantially therapeutically inactive.

7. The composition of claim 1, wherein the at least one of $R^5$ or $R^6$ which acts as a therapeutically active compound, or a precursor of a therapeutically active compound, when dissociated from platinum, has a molecular weight of less than about 800 g/mol.

8. The composition of claim 1, wherein the at least one of $R^5$ or $R^6$, which acts as a therapeutically active compound, or a precursor of a therapeutically active compound, when dissociated from platinum, has a molecular weight of less than about 600 g/mol.

9. The composition of claim 1, wherein the at least one of $R^5$ or $R^6$, which acts as a therapeutically active compound, or a precursor of a therapeutically active compound, when dissociated from platinum, has a molecular weight of less than about 400 g/mol.

10. The composition of claim 1, wherein the at least one of $R^5$ or $R^6$, which acts as a therapeutically active compound, or a precursor of a therapeutically active compound, when dissociated from platinum, has a molecular weight of less than about 300 g/mol.

11. The composition of claim 1, wherein the at least one of $R^5$ or $R^6$, which acts as a therapeutically active compound, or a precursor of a therapeutically active compound, when dissociated from platinum, has a molecular weight of less than about 200 g/mol.

12. The composition of claim 1, wherein the at least one of $R^5$ or $R^6$, which acts as a therapeutically active compound, or a precursor of a therapeutically active compound, when dissociated from platinum, has a molecular weight of less than about 100 g/mol.

13. The composition of claim 1, wherein the at least one of $R^5$ or $R^6$, which acts as a therapeutically active compound, or a precursor of a therapeutically active compound, when dissociated from platinum, is directly associated with platinum center.

14. The composition of claim 1, wherein the at least one of $R^5$ or $R^6$, which acts as a therapeutically active compound, or a precursor of a therapeutically active compound, when dissociated from platinum, is associated with platinum center through a tether.

15. The composition of claim 1, wherein the therapeutically active compound is not a steroid.

16. The composition of claim 1, wherein the therapeutically active compound causes at least a ten-fold increase in cell death in a cancer cell compared to a non-cancer cell.

* * * * *